United States Patent

Hamanaka et al.

Patent Number: 5,663,417
Date of Patent: Sep. 2, 1997

[54] CARBOCYCLIC SULFONAMIDES

[75] Inventors: Nobuyuki Hamanaka, Osaka; Tsumoru Miyamoto, Shiga, both of Japan

[73] Assignee: Ono Pharmaceutical Co., Ltd., Osaka, Japan

[21] Appl. No.: 187,008

[22] Filed: Jan. 27, 1994

[30] Foreign Application Priority Data

Jan. 29, 1993 [JP] Japan ................................ 5-013021

[51] Int. Cl.$^6$ .................. A61K 31/215; A61K 31/18; C07C 69/608
[52] U.S. Cl. .................. 560/121; 560/116; 562/503; 562/507; 564/80; 564/90; 564/92; 564/95
[58] Field of Search .................... 514/535, 539, 514/550, 562, 530, 601, 602; 564/80, 90, 92, 95; 560/116, 121; 562/503, 507

[56] References Cited

U.S. PATENT DOCUMENTS 4,861,913  8/1989  Narisada ........................... 572/427
5,168,101  12/1992  Arai et al. ......................... 514/530

OTHER PUBLICATIONS

16th International Symposium on the Chemistry of Natural Products Abstracts p. 453, (1988), Lieb et al.

Primary Examiner—Marianne M. Cintins
Assistant Examiner—Dwayne C. Jones
Attorney, Agent, or Firm—Sughrue, Mion, Zinn, Macpeak & Seas

[57] ABSTRACT

(1) Prostaglandin (PG) $E_2$ antagonist or agonist containing carbocyclic sulfonamides represented by the compound of the formula (I):

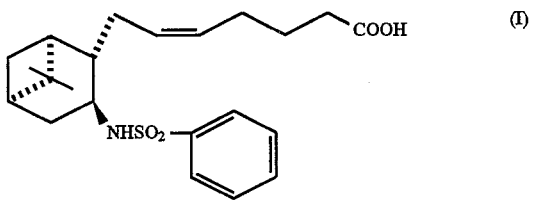

cyclodextrin clathrates thereof, non-toxic salts thereof as active ingredient, (2) carbocyclic sulfonamides represented by the compound of the formula (II):

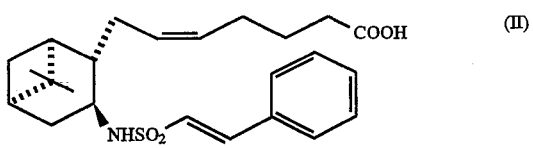

cyclodextrin clathrates thereof, non-toxic salts thereof, (3) process for the preparation of the compound represented by the compound of the formula (II) described hereinbefore, (4) $PGE_2$ antagonist or agonist containing the compound represented by the compound of the formula (II) as active ingredient.

The compounds represented by the compounds of the formula (I) and (II) can be adapted to medicines which possess an inhibitory effect of uterine contraction, an analgetic action, an inhibitory effect of digestive peristalsis, a sleep-inducing effect as $PGE_2$ antagonists, and an uterine contractile activity, a promoting effect of digestive peristalsis, a suppressive effect of gastric acid secretion, a hypotensive activity as $PGE_2$ agonists, because they bind onto $PGE_2$ receptor and have an activity of antagonist or agonist against the action thereof.

23 Claims, No Drawings

CARBOCYCLIC SULFONAMIDES

SUMMARY

This invention is related to carbocyclic sulfonamides. More particularly, this invention is related to:

(1) prostaglandin $E_2$ antagonists or agonists which comprises carbocyclic sulfonamides of the formula:

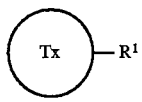   (Ix)

wherein all the symbols are the same meaning as hereafter defined, as active ingredient, (2)-1 carbocyclic sulfonamides of the formula:

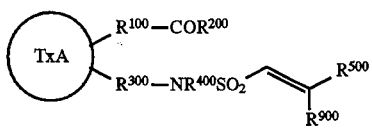   (Iy)

wherein all the symbols are the same meaning as hereafter defined, (2)-2 prostaglandin $E_2$ antagonists or agonists which comprises carbocyclic sulfonamides of the formula (Iy) as active ingredient and (2)-3 process for the preparation of carbocyclic sulfonamides of the formula (Iy).

BACKGROUND

As prostaglandin (PG)$E_2$ agonists, many compounds have been known including $PGE_2$ per se or its derivatives. However, no compounds which antagonize for $PGE_2$ or inhibit $PGE_2$ activity have been known until now.

$PGE_2$ has been known as a metabolite in the arachidonate cascade. It has been known that $PGE_2$ has uterine contractile activity, a pain-inducing effect, a promoting effect of digestive peristalsis, an awaking effect, a suppressive effect of gastric acid secretion, a hypotensive activity etc.

To antagonize $PGE_2$ means to suppress the effects above mentioned, so $PGE_2$ antagonists are considered to inhibit uterine contraction, to have an analgetic action, to inhibit digestive peristalsis, to induce sleep. Therefor, $PGE_2$ antagonists are considered to be useful for analgesics, antidiarrheals, sleep inducer or for the preventive of abortion.

To agonize for $PGE_2$ means to promote the effects above mentioned, so $PGE_2$ agonists are considered to have a uterine contractile activity, to promote digestive peristalsis, to suppress gastric acid secretion, to lower blood pressure. Therefor, $PGE_2$ agonists are considered to be useful for abortient, cathartics, antiulcer, anti-gastritis, antihypertensive.

RELATED ARTS

The compound of the formula (Ix) used in the present invention was disclosed to be useful for thromboxane $A_2$ ($TxA_2$) antagonists in the specification of the U.S. Pat. No. 5,168,101 and the U.S. Pat. No. 4,861,913.

These specifications disclose the following each compounds.

That is, the specification of the U.S. Pat. No. 5,168,101 discloses sulfonamide compounds of the formula:

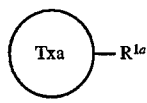   (AA)

wherein $R^{1a}$ is
 i) $COOR^{11a}$,
 ii) $CH_2OR^{12a}$ or
 iii) $CONR^{13a}R^{14a}$ in which $R^{11a}$ is hydrogen, C1-20 alkyl, carbocyclic ring unsubstituted or substituted by C1-4 alkyl, alkoxy or halogen, or steroid;

$R^{12a}$ is hydrogen or $COR^{15a}$;

$R^{13a}$ and $R^{14a}$ each, independently, is hydrogen, C1-4 alkyl or $NR^{13a}R^{14a}$ is amino acid residue or heterocyclic ring;

$R^{15a}$ is C1-4 alkyl or phenyl;

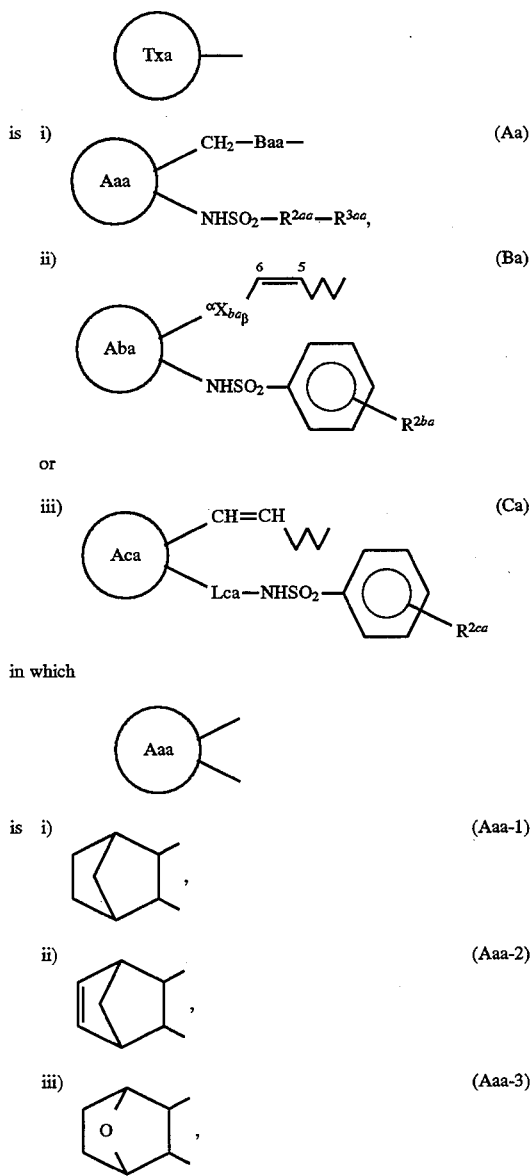

iv)  (Aaa-4)

v)  (Aaa-5)

vi) 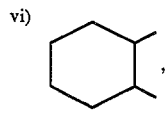 (Aaa-6)

vii) 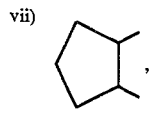 (Aaa-7)

viii) 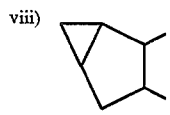 (Aaa-8)

ix) 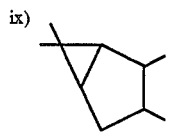 (Aaa-9)

x) 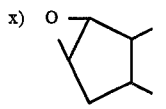 (Aaa-10)

or xi) 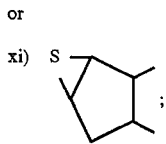 (Aaa-11)

Baa is
i) —CH$_2$—CH$_2$(CH$_2$)$_{ma}$— (Baa-1),
ii) cis—CH=CH—(CH$_2$)$_{ma}$— (Baa-2),
iii) —CH$_2$—O—(CH$_2$)$_{ma}$— (Baa-3),
iv) —S—(CH$_2$)$_{ma}$— (Baa-4) or
v)

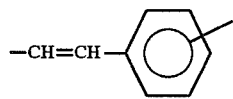 (Baa-5)

in which ma is 1–6, a double bond is E, Z and EZ mixture and phenylene is o-, m- or p-phenylene in the formula (Baa-5);

R$^{2aa}$ is a single bond or C1–4 alkylene;

R$^{3aa}$ is carbocyclic ring or heterocyclic ring unsubstituted or substituted by one to three of C1–4 alkyl, C1–4 alkoxy, hydroxy, carboxyl, cyano, halogen or nitro or R$^{2aa}$ and R$^{3aa}$ taken together, is C1–12 alkyl;

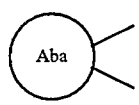

is i)  (Aba-1)

ii) 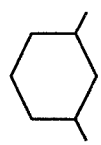 (Aba-2)

iii) 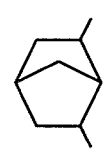 (Aba-3)

or iv) 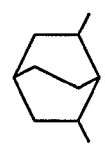 (Aba-4)

Xba is
i) a single bond,
ii) C1–4 alkylene or
iii) C2–4 alkenylene, with the proviso that, $^\alpha$CH=CHCH$_2^\beta$ and $^\alpha$CH$_2$CH=CHCH$_2^\beta$ are excluded;

R$^{2ba}$ is
i) hydrogen,
ii) halogen or
iii) C1–4 alkyl;

the configuration of a double bond between C5–C6 in the formula (Ba) is cis;

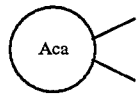

is i)  (Aca-1)

ii)  (Aca-2)

iii) 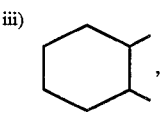 (Aca-3)

iv)  (Aca-4)

-continued v) 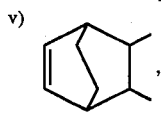 (Aca-5)

vi) 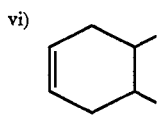 (Aca-6)

vii) 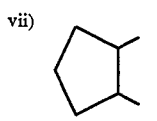 (Aca-7)

or viii) 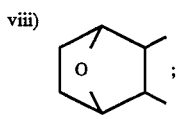 (Aca-8)

Lca is C1–4 alkylene;

$R^{2ca}$ is hydrogen, C1–4 alkyl or halogen;

the configuration of a double bond between C5–C6 in the formula (Ca) is cis or trans;

with the proviso that, when

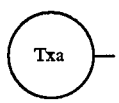

is the formula (Aa), $R^{11a}$ is not hydrogen and C1–20 alkyl;

cyclodextrin clathrates thereof and non-toxic acid salts thereof, when $R^{11a}$ is hydrogen or $NR^{13a}R^{14a}$ is amino acid residue.

The specification of the U.S. Pat. No. 4,861,913 discloses bicyclosulfonamide derivatives of the formula:

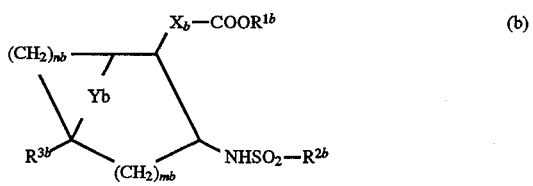 (b)

wherein $R^{1b}$ is hydrogen or lower alkyl (C1–8);

$R^{2b}$ is alkyl, aryl or substituted aryl, aralkyl or heterocyclic ring;

$R^{3b}$ is hydrogen or methyl;

Xb is alkylene or alkenylene which may be substituted fluorine or contained oxygen, sulfur and/or phenylene in the chain;

Yb is straight or branched alkylene or alkenylene, oxygen or sulfur;

mb is 0 or 1;

nb is 0, 1 or 2;

and salts thereof.

Further, Bayer AG published the following compound in International Symposium on the chemistry of Natural Products at from May, 29 to Jun. 3, 1988.

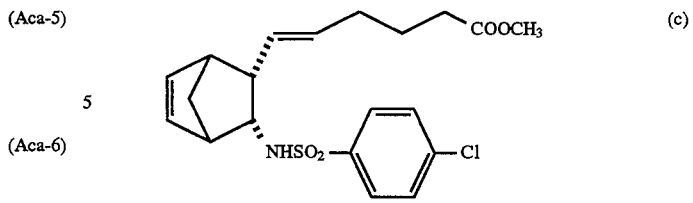 (c)

COMPARISON WITH THE RELATED ARTS

As mentioned above, the compounds of the formula (Ix), except for a part thereof, are overlapped with those of the formulae (a), (b) and (c) described in related arts.

However, the compounds Of the formula (a), (b) and (c) are disclosed only to be useful for $TXA_2$ antagonist. The disclosure does not suggest the use as $PGE_2$ antagonists or agonists which is made clear in the present invention.

$TXA_2$ has been known to have activities of platelet aggregation, aorta contraction, thrombi formation, etc., and therefore, $TXA_2$ antagonist is considered to be useful for antiinflammatory agents, antithrombotic agents, treatment of cardiac infraction.

Meanwhile, as mentioned above $PGE_2$ has been known to have an uterine contractile activity, a pain-inducing effect, a promoting effect of digestive peristalsis, an awaking effect, a suppressive effect of gastric acid secretion, a hypotensive activity etc. Therefor, $PGE_2$ antagonists are considered to inhibit uterine contraction, to have an analgetic action, to inhibit digestive peristalsis, to induce sleep, and $PGE_2$ agonists are considered to have uterine contractile activity, to promote digestive peristalsis, to suppress gastric acid secretion, to blood pressure.

As understood from the above fact, $PGE_2$ antagonist or agonist differs from $TXA_2$ antagonist in active site, mechanism, application and property thereof. So it is difficult to expect that compounds have both actions at the same time.

The compounds of the formula (Iy) of the present invention differ from those of the formulae (a), (b) and (c) in the structure and the pharmacological action thereof. So the compound of the formula (Iy) can not be expected easily from these compounds.

That is, in the structural view point, all the compounds of the formula (Iy) have a double bond between a sulfonamide group ($NR^{400}$—$SO_2$) and the end of ω-chain ($R^{500}$). The compounds differ from the compounds of the formulae (a), (b) and (c) in this point.

In the pharmacological view point, $PGE_2$ antagonism or $PGE_2$ agonism has nothing to do with $TXA_2$ antagonism. Therefore, $PGE_2$ antagonism or $PGE_2$ agonism of the compound of the formula (Iy) can not be expected from $TXA_2$ antagonism of the compound of the formulae (a), (b) and (c). There is no suggestion in any of the related arts mentioned above that $PGE_2$ antagonism or $PGE_2$ agonism is maintained even though a double bond is introduced in ω-chain.

DISCLOSURE OF THE INVENTION

The present invention is related to a novel use of known compounds, novel compounds, process for the preparation of the novel compounds and a use of the novel compounds.

Accordingly, the present invention is related to (1) prostaglandin $E_2$ antagonists or $PGE_2$ agonists which comprises carbocyclic sulfonamides of the formula:

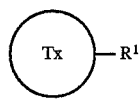 (Ix)

wherein R¹ is
i) COOR¹¹ or
ii) CONR¹³R¹⁴ in which R¹¹ is hydrogen, C1–20 alkyl;

R¹³ and R¹⁴ each, independently, is hydrogen, C1–4 alkyl or

NR¹³R¹⁴ is amino acid residue;

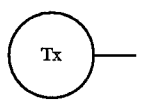

is i)

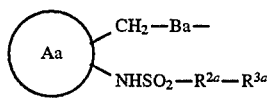 (A)

ii)

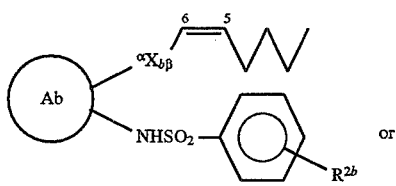 (B)

or iii)

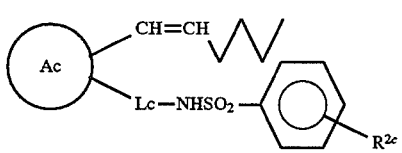 (C)

in which

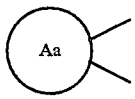

is i)

 (Aa-1)

ii)

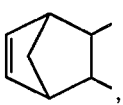 (Aa-2)

iii)

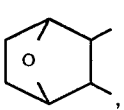 (Aa-3)

-continued iv)

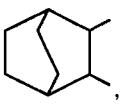 (Aa-4)

v)

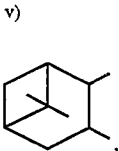 (Aa-5)

vi)

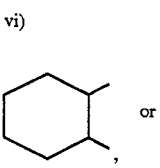 or (Aa-6)

vii)

 (Aa-7)

Ba is
i) —CH₂—CH₂(CH₂)ₘ— (Ba-1) or
ii) cis—CH=CH—(CH₂)ₘ— (Ba-2)

in which m is 1–6;

R²ᵃ is a single bond or C1–4 alkylene;

R³ᵃ is benzene, naphthalene or C4–7 cycloalkyl unsubstituted or substituted by one to three of C1–4 alkyl, C1–4 alkoxy, hydroxy, cyano, halogen, trifluoromethyl or nitro or R²ᵃ and R³ᵃ taken together, is C1–12 alkyl;

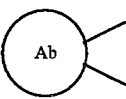

is i)

 (Ab-1)

ii)

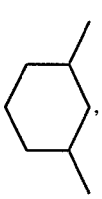 (Ab-2)

iii)

or iv)

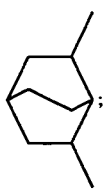

Xb is
i) a single bond,
ii) C1–4 alkylene or
iii) C2–4 alkenylene, with the proviso that, $^{\alpha}CH=CHCH_2^{\beta}$ and $^{\alpha}CH_2CH=CHCH_2^{\beta}$ are excluded;

$R^{2b}$ is hydrogen, C1–4 alkyl, C1–4 alkoxy, hydroxy, cyano, halogen, trifluoromethyl or nitro;

the configuration of a double bond between C5–C6 in the formula (B) is cis;

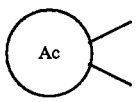

is i)

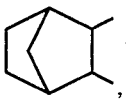 (Ac-1)

ii)

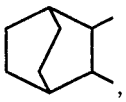 (Ac-2)

iii)

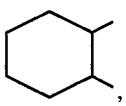 (Ac-3)

iv)

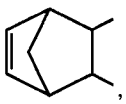 (Ac-4)

v)

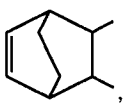 (Ac-5)

vi)

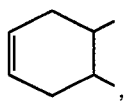 (Ac-6)

vii)

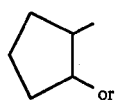 (Ac-7)

viii)

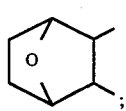 (Ac-8)

Lc is C1–4 alkylene;

$R^{2c}$ is hydrogen, C1–4 alkyl, C1–4 alkoxy, hydroxy, cyano, halogen, trifluoromethyl or nitro;

the configuration of a double bond between C5–C6 in the formula (c) is cis or trans;

cyclodextrin clathrates thereof or non-toxic acid salts thereof, when $R^{11}$ is hydrogen or $NR^{13}R^{14}$ is amino acid residue, as active ingredient, (2)-1 carbocyclic sulfonamides of the formula:

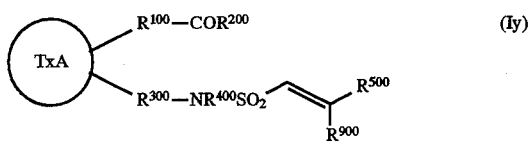 (Iy)

wherein

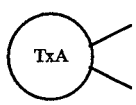

is i)

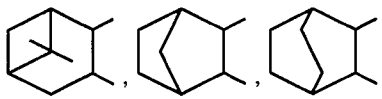

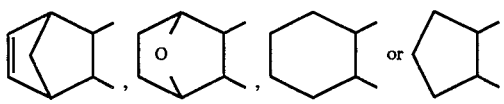

or ii)

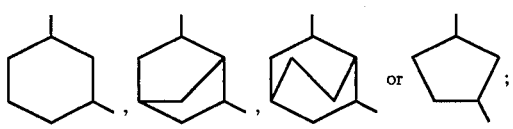

$R^{100}$ is C4–7 alkylene or C4–7 alkenylene;

$R^{200}$ is hydroxy, C1–20 alkoxy or $NR^{230}R^{240}$ in which $R^{230}$ and $R^{240}$ each, independently, is hydrogen, C1–4 alkyl or $NR^{230}R^{240}$ is amino acid residue;

$R^{300}$ is a single bond or C1–4 alkylene;

$R^{400}$ is hydrogen or C1–4 alkyl;

$R^{500}$ and $R^{900}$ each, independently, is i)

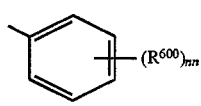

in which $R^{600}$ is hydrogen, C1–4 alkyl, C1–4 alkoxy, hydroxy, halogen, trifluoromethyl, nitro;
nn is 1, 2 or 3;

ii)

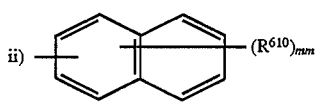

in which $R^{610}$ is hydrogen, C1–4 alkyl, C1–4 alkoxy, hydroxy, halogen, trifluoromethyl, nitro;
mm is 1, 2 or 3;

iii)

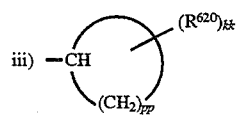

in which $R^{620}$ is hydrogen, C1–4 alkyl, C1–4 alkoxy, hydroxy, halogen, trifluoromethyl, nitro;
kk is 1, 2 or 3;
pp is 3, 4, 5, or 6;
iv) C1–7 alkyl or
v) hydrogen;
cyclodextrin ₁clathrates thereof or non-toxic salts thereof, (2)-2 process for the preparation of the compounds of the formula (Iy) and (2)-3 prostaglandin $E_2$ antagonists or agonists which comprises the compounds of the formula (Iy) as active ingredient.

The terms of alkyl, alkylene, alkenylene and alkoxy in description of each symbol throughout the present specification including claims mean straight-chain or branched-chain alkyl, alkylene, alkenylene and alkoxy. The configuration of double bonds in alkenylene are E, Z and E, Z mixtures.

The presence of asymmetric centers leads, as is well known, to the existence of isomers. And all optical isomers and all mixtures thereof are included in the formula (Ix) and (Iy). For instance, a mixture of one optical isomer and enantiomer thereof, a racemate which is an equivalent mixture especially and a mixture of one optical isomer and diastereomer thereof are also included.

In the structural formula throughout the present specification dotted line ( ---- )

indicate α-configuration, tapered line ( ◀ )

indicate β-configuration.

In the formula (Ix) and (Iy), for example, the ring structures of the formula:

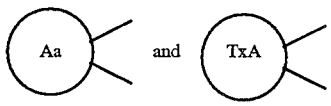

is named each and numbered at each position as follows.

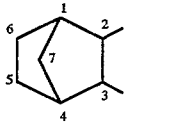

bicyclo[2.2.1]heptane, (Aa-1)

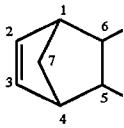

bicyclo[2.2.1]hept-2-ene, (Aa-2)

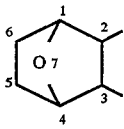

7-oxa-bicyclo[2.2.1]heptane, (Aa-3)

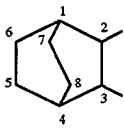

bicyclo[2.2.2]octane, (Aa-4)

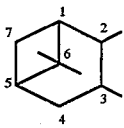

6,6-dimethylbicyclo[3.3.1]heptane, (Aa-5)

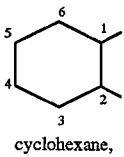

cyclohexane, (Aa-6)

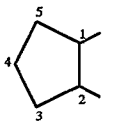

cyclopentane (Aa-7)

As will be apparent to those skilled in the art, the ring structures described above have two [in case of the formula (Aa-4), (Aa-6) and (Aa-7)] or four [in case of the formula (Aa-1), (Aa-2), (Aa-3) and (Aa-5)] asymmetric carbons. Namely, they are 1-, 2-, 3- and 4-position carbons in the formula (Aa-1) and (Aa-3), 1-, 4-, 5- and 6-position carbons in the formula (Aa-2), 2- and 3-position carbons in the formulae (Aa-4), 1- and 2-position carbons in the formula (Aa-6) and (Aa-7) and 1-, 2-, 3- and 5-position carbons in the formula (Aa-5).

And, in the formula (Ix) and (Iy), the ring structures of the formula:

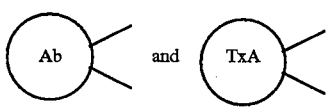

is named each and numbered at each position as follows.

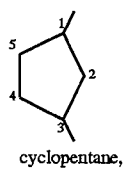
(Ab-1)

cyclopentane,

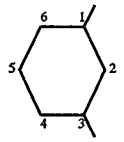
(Ab-2)

cyclohexane,

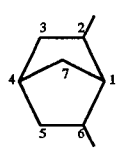
(Ab-3)

bicyclo[2.2.1]heptane,

(Ab-4)

bicyclo[2.2.1]octane

As will be apparent to those skilled in the art, the ring structures described above have asymmetric carbons. Namely, the ring structures of the formula (Ab-1) and (Ab-2) have two asymmetric carbons (1- and 3-position carbons), and the ring structures of the formula (Ab-3) and (Ab-4) have four asymmetric carbons (1-, 2-, 4- and 6-position carbons).

And, in the formula (Ix), the ring structures of the formula:

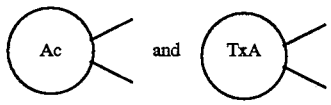

is named each and numbered at each position as follows.

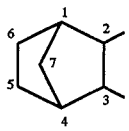
(Ac-1)

bicyclo[2.2.1]heptane,

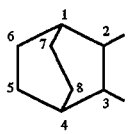
(Ac-2)

bicyclo[2.2.2]octane,

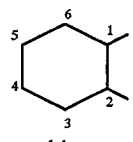
(Ac-3)

cyclohexane,

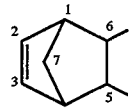
(Ac-4)

bicyclo[2.2.1]hept-2-ene,

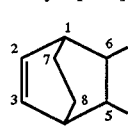
(Ac-5)

bicyclo[2.2.2]oct-2-ene,

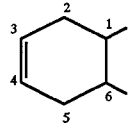
(Ac-6)

cyclohex-3-ene,

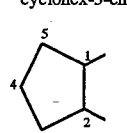
(Ac-7)

cyclopentane,

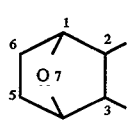
(Ac-8)

7-oxa-bicyclo[2.2.1]heptane

As will be apparent to those skilled in the art, the ring structures described above have two [in case of the formula (Ac-2), (Ac-3), (Ac-6) and (Ac-7)] or four [in case of the formula (Ac-1), (Ac-4), (Ac-5) and (Ac-8)] asymmetric carbons. Namely, they are 2- and 3-position carbons in the formula (Ac-2), 1- and 2-position carbons in the formula (Ac-3) and (Ac-7), 1- and 6-position carbons in the formula (Ac-6), 1-, 2-, 3- and 4-position carbons in the formula (Ac-1) and (Ac-8), 1-, 4-, 5- and 6-position carbons in the formula (Ac-4) and (Ac-5).

The steric structures of each isomers or racemates are shown by absolute configuration, for example, as follows.

(i) in case of an optically active substance

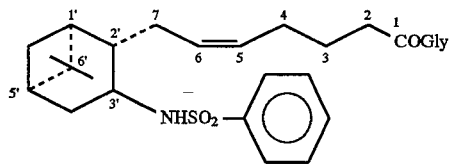

amide of (5Z)-7-[(1S,2S,3S,5R)-3-phenylsulfonylamino-6,6-dimethylbicyclo [3.1.1] heptan-2-yl]hept-5-enoic acid and glycine

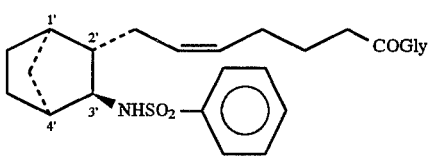

amide of (5Z)-7-[(1R,2S,3S,4S)-3-phenylsulfonylaminobicyclo[2.2.1]heptan-2-yl]hept-5-enoic acid and glycine

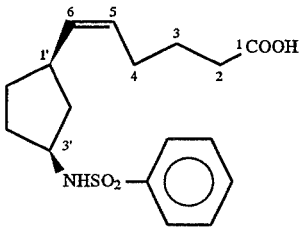

(5Z)-6-[(1R,3S)-3-phenylsulfonylaminocyclopentyl]hex-5-enoic acid

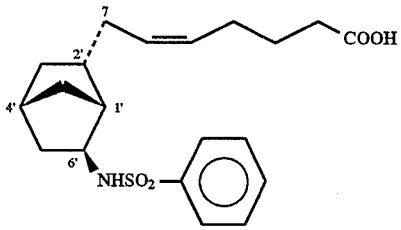

(5Z)-7-[(1R,2R,4R,6S)-6-phenylsulfonylaminobicyclo[2.2.1]heptan-2-yl]hept-5-enoic acid (ii) in case of racemate

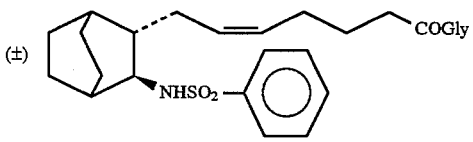

amide of (5Z)-7-[(2S*,3S*)-3-phenylsulfonylaminobicyclo[2.2.2]octan-2-yl]hept-5-enoic acid and glycine

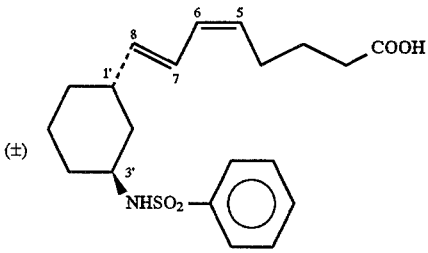

(5Z,7E)-8-[(1S*,3S*)-3-phenylsulfonylaminocyclohexyl]oct-5,7-dienoic acid

In the formula (Ix), C1–20 alkyl represented by $R^{11}$ means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and isomeric groups thereof. Preferable $R^{11}$ are methyl, ethyl, propyl, isopropyl, 1-ethylpropyl, hexyl, octyl, decyl, dodecyl. It's also preferable that $R^{11}$ is hydrogen.

In the formula (Ix), C1–4 alkyl represented by $R^{13}$ and $R^{14}$ means methyl, ethyl, propyl, butyl and isomeric groups thereof.

In the formula (Ix), amino acid residues represented by $NR^{13}R^{14}$ mean α-amino acid residues wherein a hydrogen in the amino is removed. For example, they are glycine, alanine, valine, isoleucine, leucine, serine, threonine, proline, asparagine, glutamine, methionine, phenylalanine, tyrosine, aspartic acid, glutamic acid or lysine residue. Preferable amino acid residue are glycine, alanine, glutamic acid, lysine residue.

Preferable the ring structure of the formula:

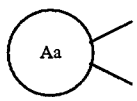

is bridged rings represented by the formula (Aa-1), (Aa-4), (Aa-5), (Aa-6) and (Aa-7).

In the formula (Ix), out of groups represented by Ba, the formula (Ba-2) having a double bond is preferred.

In the formula (Ix), the formula —$(CH_2)_m$— means methylene, ethylene, trimethylene, tetramethylene, pentamethylene and hexamethylene, and preferable group is trimethylene.

In the formula (Ix), $R^{2a}$ means a single bond or C1–4 alkyl. C1–4 alkyl means methyl, ethyl, propyl, butyl and isomeric groups thereof. Preferable $R^{2a}$ is a single bond.

In the formula (Ix), C4–7 cycloalkyl represented by $R^{3a}$ means cyclobutyl, cyclopentyl, cyclohexyl, cycloheptyl.

In the formula (Ix), C1–4 alkyl represented by substituents in $R^{3a}$ means methyl, ethyl, propyl, butyl and isomeric groups thereof, C1–4 alkoxy means methoxy, ethoxy, propoxy, butoxy and isomeric groups thereof, and halogen means fluorine, chlorine, iodine and bromine.

In the formula (Ix), C1–12 alkyl represented by $R^{2a}$ and $R^{3a}$ taken together means methyl, ethyl, propyl, butyl, pentyl, hexyl, heptyl, octyl, nonyl, decyl, undecyl, dodecyl and isomeric groups thereof, and all groups are preferable.

All the rings represented by the formula:

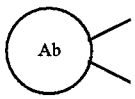

are preferable.

In the formula (Ix), C1–4 alkylene represented by Xb means methylene, ethylene, trimethylene, tetramethylene and isomeric groups thereof.

In the formula (Ix), C2–4 alkenylene represented by Xb means vinylene, propenylene, butenylene, butadienylene and isomeric groups thereof.

Preferable Xb is a single bond, methylene, ethylene and vinylene. Especially preferable group is a single bond.

In the formula (Ix), C1–4 alkyl represented by $R^{2b}$ means methyl, ethyl, propyl, butyl and isomeric groups thereof, C1–4 alkoxy represented by $R^{2b}$ means methoxy, ethoxy, propoxy, butoxy and isomeric groups thereof, and halogen means fluorine, chlorine, iodine and bromine and all groups are preferable. It's also preferable that $R^{2b}$ is hydrogen.

Preferable the ring structure of the formula:

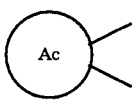

is the groups represented by the formula (Ac-1), (Ac-3), (Ac-4) and (Ac-7).

In the formula (Ix), C1–4 alkylene represented by LC means methylene, ethylene, trimethylene and tetramethylene, and preferable groups are methylene and ethylene.

In the formula (Ix), C1–4 alkyl represented by $R^{2c}$ means methyl, ethyl, propyl, butyl and isometric groups thereof, and preferable groups is methyl. C1–4 alkoxy represented by $R^{2c}$ means methoxy, ethoxy, propoxy, butoxy and isomeric groups thereof. Halogen represented by $R^{2c}$ means fluorine, chlorine, bromine and iodine and preferable group is bromine.

In the formula (Iy), C4–7 alkylene represented by $R^{100}$ means tetramethylene, pentamethylene, hexamethylene, heptamethylene and isomeric groups thereof.

In the formula (Iy), C4–7 alkenylene represented by $R^{100}$ means butenylene, pentenylene, hexenylene, heptenylene and isomeric groups thereof.

Preferable $R^{100}$ is pentamethylene, hexamethylene, pentenylene and hexenylene.

In the formula (Iy), C1–20 alkoxy represented by $R^{200}$ means methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, icosyloxy and isomeric groups thereof.

In the formula (Iy), C1–4 alkyl represented by $R^{230}$ and $R^{240}$ means methyl, ethyl, propyl, butyl and isomeric groups thereof.

In the formula (Iy), amino acid residues represented by $NR^{230}N^{240}$ mean α-amino acid residues wherein a hydrogen in the amino is removed. For example, they are glycine, alanine, valine, isoleucine, leucine, serine, threonine, proline, asparagine, glutamine, methionine, phenylalanine, tyrosine, aspartic acid, glutamic acid or lysine residue.

In the formula (Iy), C1–4 alkylene represented by $R^{300}$ means methylene, ethylene, trimethylene, tetramethylene and isomeric groups thereof.

Preferable $R^{300}$ is a single bond and methylene.

In the formula (Iy), C1–4 alkyl represented by $R^{400}$ means methyl, ethyl, propyl, butyl and isomeric groups thereof.

Preferable $R^{400}$ is hydrogen and methyl.

In the formula (Iy), C1–4 alkyl represented by $R^{600}$, $R^{610}$ and $R^{620}$ means methyl, ethyl, propyl, butyl and isomeric groups thereof.

In the formula (Iy), C1–4 alkoxy represented by $R^{600}$, $R^{610}$ and $R^{620}$ means methoxy, ethoxy, propoxy, butoxy and isomeric groups thereof.

In the formula (Iy), halogen represented by $R^{600}$, $R^{610}$ and $R^{620}$ means fluorine, chlorine, bromine and iodine.

Preferable $R^{600}$, $R^{610}$ and $R^{620}$ are hydrogen, fluorine, chlorine, bromine, iodine, methyl, methoxy, nitro and trifluoromethyl.

In the formula (Iy), the formula:

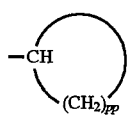

means cyclobutyl, cyclopentyl, cyclohexyl and cycloheptyl, and preferable group is cyclohexyl.

In the formula (Iy), C1–7 alkyl represented by $R^{500}$ and $R^{900}$ means methyl, ethyl, propyl, butyl, pentyl, hexyl, heptyl and isomeric groups thereof.

Preferable Compounds

In the compounds of the present invention of the formula (Ix), the compounds described in Example and the following compounds are preferable.

7-[3-(2-Naphtyl)sulfonylaminobicyclo[2.2.1]heptan-2-yl]-5-heptenoic acid,

7-[3-(2-Cyclohexylethyl)sulfonylaminobicyclo[2.2.1]heptan-2-yl]-5-heptenoic acid, 7-[3-Hexylsulfonylaminobicyclo[2.2.1]heptan-2-yl]-5-heptenoic acid, 7-[5-(4-Methylphenyl)sulfonylaminobicyclo[2.2.1]-2-heptan-6-yl]-5-heptenoic acid, 7-[5-(2-Naphtyl)sulfonylaminobicyclo[2.2.1]-2-heptan-6-yl]-5-heptenoic acid, 7-[5-(2-Cyclohexylethyl)sulfonylaminobicyclo[2.2.1]-2-heptan-6-yl]-5-heptenoic acid, 7-[5-Hexylsulfonylaminobicyclo[2.2.1]-2-heptan-6-yl]-5-heptenoic acid, 7-[3-(4-Methylphenyl)sulfonylamino-7-oxa-bicyclo[2.2.1]heptan-2-yl]-5-heptenoic acid, 7-[3-(2-Naphtyl)sulfonylamino-7-oxa-bicyclo[2.2.1]heptan-2-yl]-5-heptenoic acid, 7-[3-(2-Cyclohexylethyl sulfonylamino)-7-oxa-bicyclo[2.2.1]heptan-2-yl]-5-heptenoic acid, 7-[3-Hexylsulfonylamino-7-oxa-bicyclo[2.2.1]heptan-2-yl]-5-heptenoic acid, 7-[3-(2-Naphtyl)sulfonylaminobicyclo[2.2.2]octan-2-yl]-5-heptenoic acid, 7-[3-(2-Cyclohexylethyl)sulfonylaminobicyclo[2.2.2]octan-2-yl]-5-heptenoic acid, 7-[3-Hexylsulfonylaminobicyclo[2.2.2]octan-2-yl]-5-heptenoic acid, 7-[3-(4-Methylphenyl)sulfonylamino-6,6-dimethylbicyclo[3.1.1]heptan-2-yl]-5-heptenoic acid, 7-[2-(4-Methylphenyl)sulfonylaminocyclohexyl]-5-heptenoic acid, 7-[2-(2-Naphtyl)sulfonylaminocyclohexyl]-5-heptenoic acid, 7-[2-(2-Cyclohexylethyl)sulfonylaminocyclohexyl]-5-heptenoic acid, 7-[2-Hexylsulfonylaminocyclohexyl]-5-heptenoic acid, 7-[2-(2-Naphtyl)sulfonylaminocyclohexyl]-5-heptenoic acid, 7-[2-(2-Cyclohexylethyl)sulfonylaminocyclopentyl]-5-heptenoic acid, 7-[2-Hexylsulfonylaminocyclopentyl]-5-heptenoic acid, 6-[3-(4-Methylphenyl)sulfonylaminocyclopentyl]-5-hexenoic acid, 7-[3-(4-Methylphenyl)sulfonylaminocyclopentyl]-5-heptenoic acid, 8-[3-(4-Methylphenyl)sulfonylaminocyclopentyl]-5,7-octadienoic acid, 6-[3-(4-Methylphenyl)sulfonylaminocyclohexyl]-5-hexenoic acid, 7-[3-(4-Methylphenyl)sulfonylaminocyclohexyl]-5-heptenoic acid, 8-[3-(4-Methylphenyl)sulfonylaminocyclohexyl]-5,7-octadienoic acid, 6-[6-(4-Methylphenyl)sulfonylaminobicyclo[2.2.1]heptan-2-yl]-5-hexenoic acid, 7-[6-(4-Methylphenyl)sulfonylaminobicyclo[2.2.1]heptan-2-yl]-5-heptenoic acid, 8-[6-(4-Methylphenyl)sulfonylaminobicyclo[2.2.1]heptan-2-yl]-5,7-octadienoic acid, 6-[6-(4-Methylphenyl)sulfonylaminobicyclo[2.2.2]octan-2-yl]-5-hexenoic acid, 7-[6-(4-Methylphenyl)sulfonylaminobicyclo[2.2.2]octan-2-yl]-5-heptenoic acid, 8-[6-(4-Methylphenyl)sulfonylaminobicyclo[2.2.2]octan-2-yl]-5,7-octadienoic acid, 6-[3-(4-Methylphenyl)sulfonylaminomethylbicyclo[2.2.1]heptan-2-yl]-5-hexenoic acid, 6-[3-(4-Methylphenyl)sulfonylaminomethylbicyclo[2.2.2]octan-2-yl]-5-hexenoic acid, 6-[2-(4-Methylphenyl)sulfonylaminomethylcyclohexyl]-5-hexenoic acid, 6-[5-(4-Methylphenyl)sulfonylaminomethylbicyclo[2.2.1]-2-hepten-6-yl]-5-hexenoic acid, 6-[5-(4-Methylphenyl)sulfonylaminomethylbicyclo[2.2.2]-2-octen-6-yl]-5-hexenoic acid, 6-[6-(4-Methylphenyl)sulfonylaminomethyl-3-cyclohexenyl]-5-hexenoic acid, 6-[2-(4-Methylphenyl)sulfonylaminomethylcyclopentyl]-5-hexenoic acid, 6-[3-(4-Methylphenyl)sulfonylaminomethyl-7-oxa-bicyclo[2.2.1]heptan-2-yl]-5-hexenoic acid, and ester, amido, amido with amino acid thereof.

In the compounds of the present invention of the formula (Iy), the compounds described in the Examples and the following compounds are preferable.

Esters, amides amides with amino acid of example compounds,

7-[3-[2-(4-Fluorophenyl)vinylsulfonylamino]bicyclo[2.2.1]heptan2-yl]-5-heptenoic acid, 7-[3-[2-(3-Fluorophenyl)vinylsulfonylamino]bicyclo[2.2.1]heptan2-yl]-5-heptenoic acid, 7-[3-[2-(4-Chlorophenyl)vinylsulfonylamino]bicyclo[2.2.1]heptan-2-yl]-5-heptenoic acid, 7-[3-[2-(3-Chlorophenyl)vinylsulfonylamino]bicyclo[2.2.1]heptan-2-yl]-5-heptenoic acid, 7-[3-[2-(4-Bromophenyl)vinylsulfonylamino]bicyclo[2.2.1]heptan-2-yl]-5-heptenoic acid, 7-[3-[2-(3-Bromophenyl)vinylsulfonylamino]bicyclo[2.2.1]heptan-2-yl]-5-heptenoic acid, 7-[3-[2-(4-Iodophenyl)vinylsulfonylamino]bicyclo[2.2.1]heptan-2-yl]-5-heptenoic acid, 7-[3-[2-(3-Iodophenyl)vinylsulfonylamino]bicyclo[2.2.1]heptan-2-yl]-5-heptenoic acid, 7-[3-[2-(4-Methylphenyl)vinylsulfonylamino]bicyclo[2.2.1]heptan-2-yl]-5-heptenoic acid, 7-[3-[2-(3-Methylphenyl)vinylsulfonylamino]bicyclo[2.2.1]heptan-2-yl]-5-heptenoic acid, 7-[3-[2-(4-Nitrophenyl)vinylsulfonylamino]bicyclo[2.2.1]heptan-2-yl]-5-heptenoic acid, 7-[3-[2-(3-Nitrophenyl)vinylsulfonylamino]bicyclo[2.2.1]heptan-2-yl]-5-heptenoic acid, 7-[3-[2-(4-Methoxyphenyl)vinylsulfonylamino]bicyclo[2.2.1]heptan-2-yl]-5-heptenoic acid, 7-[3-[2-(3-Methoxyphenyl)vinylsulfonylamino]bicyclo[2.2.1]heptan-2-yl]-5-heptenoic acid, 7-[3-[2-(4-Trifluoromethylphenyl)vinylsulfonylamino]bicyclo[2.2.1]heptan-2-yl]-5-heptenoic acid, 7-[3-[2-(3-Trifluoromethylphenyl)vinylsulfonylamino]bicyclo[2.2.1]heptan-2-yl]-5-heptenoic acid, 7-[3-[2-(2,2-diphenyl)vinylsulfonylamino]bicyclo[2.2.1]heptan-2-yl]-5-heptenoic acid, 6-[3-[2-(4-Fluorophenyl)vinylsulfonylamino]metylbicyclo[2.2.1]heptan-2-yl]-5-hexenoic acid, 6-[3-[2-(3-Fluorophenyl)vinylsulfonylamino]metylbicyclo[2.2.1]heptan-2-yl]-5-hexenoic acid, 6-[3-[2-(4-Chlorophenyl)vinylsulfonylamino]metylbicyclo[2.2.1]heptan-2-yl]-5-hexenoic acid, 6-[3-[2-(3-Chlorophenyl)vinylsulfonylamino]metylbicyclo[2.2.1]heptan-2-yl]-5-hexenoic acid, 6-[3-[2-(4-Bromophenyl)vinylsulfonylamino]metylbicyclo[2.2.1]heptan-2-yl]-5-hexenoic acid, 6-[3-[2-(3-Bromophenyl)vinylsulfonylamino]metylbicyclo[2.2.1]heptan-2-yl]-5-hexenoic acid, 6-[3-[2-(4-Iodophenyl)vinylsulfonylamino]metylbicyclo[2.2.1]heptan-2-yl]-5-hexenoic acid, 6-[3-[2-(3-Iodophenyl)vinylsulfonylamino]metylbicyclo[2.2.1]heptan-2-yl]-5-hexenoic acid, 6-[3-[2-(4-Methylphenyl)vinylsulfonylamino]metylbicyclo[2.2.1]heptan-2-yl]-5-hexenoic acid, 6-[3-[2-(3-Methylphenyl)vinylsulfonylamino]metylbicyclo[2.2.1]heptan-2-yl]-5-hexenoic acid, 6-[3-[2-(4-Nitrophenyl)vinylsulfonylamino]metylbicyclo[2.2.1]heptan-2-yl]-5-hexenoic acid, 6-[3-[2-(3-Nitrophenyl)vinylsulfonylamino]metylbicyclo[2.2.1]heptan-2-yl]-5-hexenoic acid, 6-[3-[2-(4-Methoxyphenyl)vinylsulfonylamino]metylbicyclo[2.2.1]heptan-2-yl]-5-hexenoic acid, 6-[3-[2-(3-Methoxyphenyl)vinylsulfonylamino]metylbicyclo[2.2.1]heptan-2-yl]-5-hexenoic acid, 6-[3-[2-(4-Trifluoromethylphenyl)vinylsulfonylamino]metylbicyclo[2.2.1]heptan-2-yl]-5-hexenoic acid, 6-[3-[2-(3-Trifluoromethylphenyl)vinylsulfonylamino]metylbicyclo[2.2.1]heptan-2-yl]-5-hexenoic acid, 6-[3-[2-(2,2-diphenyl)vinylsulfonylamino]metylbicyclo[2.2.1]heptan-2-yl]-5-hexenoic acid, 7-[2-[2-(4-Fluorophenyl)vinylsulfonylamino]cyclohexyl]-5-heptenoic acid, 7-[2-[2-(3-Fluorophenyl)vinylsulfonylamino]cyclohexyl]-5-heptenoic acid, 7-[2-[2-(4-Chlorophenyl)vinylsulfonylamino]cyclohexyl]-5-heptenoic acid, 7-[2-[2-(3-Chlorophenyl)vinylsulfonylamino]cyclohexyl]-5-heptenoic acid, 7-[2-[2-(4-Bromophenyl)vinylsulfonylamino]cyclohexyl]-5-heptenoic acid, 7-[2-[2-(3-Bromophenyl)vinylsulfonylamino]cyclohexyl]-5-heptenoic acid, 7-[2-[2-(4-Iodophenyl)vinylsulfonylamino]cyclohexyl]-5-heptenoic acid, 7-[2-[2-(3-Iodophenyl)vinylsulfonylamino]cyclohexyl]-5-heptenoic acid, 7-[2-[2-(4-Methylphenyl)vinylsulfonylamino]cyclohexyl]-5-heptenoic acid, 7-[2-[2-(3-Methylphenyl)vinylsulfonylamino]cyclohexyl]-5-heptenoic acid, 7-[2-[2-(4-Nitrophenyl)vinylsulfonylamino]cyclohexyl]-5-heptenoic acid, 7-[2-[2-(3-Nitrophenyl)vinylsulfonylamino]cyclohexyl]-5-heptenoic acid, 7-[2-[2-(4-Methoxyphenyl)vinylsulfonylamino]cyclohexyl]-5-heptenoic acid, 7-[2-[2-(3-Methoxyphenyl)vinylsulfonylamino]cyclohexyl]-5-heptenoic acid, 7-[2-[2-(4-Trifluoromethylphenyl)vinylsulfonylamino]cyclohexyl]-5-heptenoic acid, 7-[2-[2-(3-Trifluoromethylphenyl)vinylsulfonylamino]
cyclohexyl]-5-heptenoic acid,
7-[2-[2-(2,2-diphenyl)vinylsulfonylamino]cyclohexyl]-5-
heptenoic acid,
6-[3-[2-(4-Fluorophenyl)vinylsulfonylamino]cyclohexyl]-
5-hexenoic acid,
6-[3-[2-(3-Fluorophenyl)vinylsulfonylamino]cyclohexyl]-
5-hexenoic acid,
6-[3-[2-(4-Chlorophenyl)vinylsulfonylamino]cyclohexyl]-
5-hexenoic acid,
6-[3-[2-(3-Chlorophenyl)vinylsulfonylamino]cyclohexyl]-
5-hexenoic acid,
6-[3-[2-(4-Bromophenyl)vinylsulfonylamino]cyclohexyl]-
5-hexenoic acid,
6-[3-[2-(3-Bromophenyl)vinylsulfonylamino]cyclohexyl]-
5-hexenoic acid,
6-[3-[2-(4-Iodophenyl)vinylsulfonylamino]cyclohexyl]-5-
hexenoic acid,
6-[3-[2-(3-Iodophenyl)vinylsulfonylamino]cyclohexyl]-5-
hexenoic acid,
6-[3-[2-(4-Methylphenyl)vinylsulfonylamino]cyclohexyl]-
5-hexenoic acid,
6-[3-[2-(3-Methylphenyl)vinylsulfonylamino]cyclohexyl]-
5-hexenoic acid,
6-[3-[2-(4-Nitrophenyl)vinylsulfonylamino]cyclohexyl]-5-
hexenoic acid,
6-[3-[2-(3-Nitrophenyl)vinylsulfonylamino]cyclohexyl]-5-
hexenoic acid,
6-[3-[2-(4-Methoxyphenyl)vinylsulfonylamino]cyclohexyl]
-5-hexenoic acid,
6-[3-[2-(3-Methoxyphenyl)vinylsulfonylamino]cyclohexyl]
-5-hexenoic acid,
6-[3-[2-(4-Trifluoromethylphenyl)vinylsulfonylamino]
cyclohexyl]-5-hexenoic acid,
6-[3-[2-(3-Trifluoromethylphenyl)vinylsulfonylamino]
cyclohexyl]-5-hexenoic acid,
6-[3-[2-(2,2-diphenyl)vinylsulfonylamino]cyclohexyl]-5-
hexenoic acid,
6-[3-[2-(4-Fluorophenyl)vinylsulfonylamino]cyclopentyl]-
5-hexenoic acid.
6-[3-[2-(3-Fluorophenyl)vinylsulfonylamino]cyclopentyl]-
5-hexenoic acid,
6-[3-[2-(4-Chlorophenyl)vinylsulfonylamino]cyclopentyl]-
5-hexenoic acid,
6-[3-[2-(3-Chlorophenyl)vinylsulfonylamino]cyclopentyl]-
5-hexenoic acid,
6-[3-[2-(4-Bromophenyl)vinylsulfonylamino]cyclopentyl]-
5-hexenoic acid,
6-[3-[2-(3-Bromophenyl)vinylsulfonylamino]cyclopentyl]-
5-hexenoic acid,
6-[3-[2-(4-Iodophenyl)vinylsulfonylamino]cyclopentyl]-5-
hexenoic acid,
6-[3-[2-(3-Iodophenyl)vinylsulfonylamino]cyclopentyl]-5-
hexenoic acid,
6-[3-[2-(4-Methylphenyl)vinylsulfonylamino]cyclopentyl]-
5-hexenoic acid,
6-[3-[2-(3-Methylphenyl)vinylsulfonylamino]cyclopentyl]-
5-hexenoic acid,
6-[3-[2-(4-Nitrophenyl)vinylsulfonylamino]cyclopentyl]-5-
hexenoic acid,
6-[3-[2-(3-Nitrophenyl)vinylsulfonylamino]cyclopentyl]-5-
hexenoic acid,
6-[3-[2-(4-Methoxyphenyl)vinylsulfonylamino]
cyclopentyl]-5-hexenoic acid,
6-[3-[2-(3-Methoxyphenyl)vinylsulfonylamino]
cyclopentyl]-5-hexenoic acid,
6-[3-[2-(4-Trifluoromethylphenyl)vinylsulfonylamino]
cyclopentyl]-5-hexenoic acid,
6-[3-[2-(3-Trifluoromethylphenyl)vinylsulfonylamino]
cyclopentyl]-5-hexenoic acid,
6-[3-[2-(2,2-diphenyl)vinylsulfonylamino]cyclopentyl]-5-
hexenoic acid,
7-[3-(2-phenylvinylsulfonylamino)bicyclo[2.2.2]octan-2-
yl]-5-heptenoic acid,
7-[3-[2-(4-Fluorophenyl)vinylsulfonylamino]bicyclo[2.2.2]
octan-2-yl]-5-heptenoic acid,
7-[3-[2-(3-Fluorophenyl)vinylsulfonylamino]bicyclo[2.2.2]
octan-2-yl]-5-heptenoic acid,
7-[3-[2-(4-Chlorophenyl)vinylsulfonylamino]bicyclo[2.2.2]
octan-2-yl]-5-heptenoic acid,
7-[3-[2-(3-Chlorophenyl)vinylsulfonylamino]bicyclo[2.2.2]
octan-2-yl]-5-heptenoic acid,
7-[3-[2-(4-Bromophenyl)vinylsulfonylamino]bicyclo[2.2.2]
octan-2-yl]-5-heptenoic acid,
7-[3-[2-(3-Bromophenyl)vinylsulfonylamino]bicyclo[2.2.2]
octan-2-yl]-5-heptenoic acid,
7-[3-[2-(4-Iodophenyl)vinylsulfonylamino]bicyclo[2.2.2]
octan-2-yl]-5-heptenoic acid,
7-[3-[2-(3-Iodophenyl)vinylsulfonylamino]bicyclo[2.2.2]
octan-2-yl]-5-heptenoic acid,
7-[3-[2-(4-Methylphenyl)vinylsulfonylamino]bicyclo
[2.2.2]octan-2-yl]-5-heptenoic acid,
7-[3-[2-(3-Methylphenyl)vinylsulfonylamino]bicyclo
[2.2.2]octan-2-yl]-5-heptenoic acid,
7-[3-[2-(4-Nitrophenyl)vinylsulfonylamino]bicyclo[2.2.2]
octan-2-yl]-5-heptenoic acid,
7-[3-[2-(3-Nitrophenyl)vinylsulfonylamino]bicyclo[2.2.2]
octan-2-yl]-5-heptenoic acid,
7-[3-[2-(4-Methoxyphenyl)vinylsulfonylamino]bicyclo
[2.2.2]octan-2-yl]-5-heptenoic acid,
7-[3-[2-(3-Methoxyphenyl)vinylsulfonylamino]bicyclo
[2.2.2]octan-2-yl]-5-heptenoic acid,
7-[3-[2-(4-Trifluoromethylphenyl)vinylsulfonylamino]
bicyclo[2.2.2]octan-2-yl]-5-heptenoic acid,
7-[3-[2-(3-Trifluoromethylphenyl)vinylsulfonylamino]
bicyclo[2.2.2]octan-2-yl]-5-heptenoic acid,
7-[3-[2-(2,2-diphenyl)vinylsulfonylamino]bicyclo[2.2.2]
octan-2-yl]-5-heptenoic acid,
7-[5-(2-phenylvinylsulfonylamino)-2-bicyclo[2.2.1]hepten-
6-yl]-5-heptenoic acid,
7-[5-[2-(4-Fluorophenyl)vinylsulfonylamino]-2-bicyclo
[2.2.1]hepten-6-yl]-5-heptenoic acid,
7-[5-[2-(3-Fluorophenyl)vinylsulfonylamino]-2-bicyclo
[2.2.1]hepten-6-yl]-5-heptenoic acid,
7-[5-[2-(4-Chlorophenyl)vinylsulfonylamino]-2-bicyclo
[2.2.1]hepten-6-yl]-5-heptenoic acid,
7-[5-[2-(3-Chlorophenyl)vinylsulfonylamino]-2-bicyclo
[2.2.1]hepten-6-yl]-5-heptenoic acid,
7-[5-[2-(4-Bromophenyl)vinylsulfonylamino]-2-bicyclo
[2.2.1]hepten-6-yl]-5-heptenoic acid,
7-[5-[2-(3-Bromophenyl)vinylsulfonylamino]-2-bicyclo
[2.2.1]hepten-6-yl]-5-heptenoic acid,
7-[5-[2-(4-Iodophenyl)vinylsulfonylamino]-2-bicyclo
[2.2.1]hepten-6-yl]-5-heptenoic acid,
7-[5-[2-(3-Iodophenyl)vinylsulfonylamino]-2-bicyclo
[2.2.1]hepten-6-yl]-5-heptenoic acid,
7-[5-[2-(4-Methylphenyl)vinylsulfonylamino]-2-bicyclo
[2.2.1]hepten-6-yl]-5-heptenoic acid,
7-[5-[2-(3-Methylphenyl)vinylsulfonylamino]-2-bicyclo
[2.2.1]hepten-6-yl]-5-heptenoic acid,
7-[5-[2-(4-Nitrophenyl)vinylsulfonylamino]-2-bicyclo
[2.2.1]hepten-6-yl]-5-heptenoic acid,
7-[5-[2-(3-Nitrophenyl)vinylsulfonylamino]-2-bicyclo
[2.2.1]hepten-6-yl]-5-heptenoic acid,
7-[5-[2-(4-Methoxyphenyl)vinylsulfonylamino]-2-bicyclo
[2.2.1]hepten-6-yl]-5-heptenoic acid, 7-[5-[2-(3-Methoxyphenyl)vinylsulfonylamino]-2-bicyclo[2.2.1]hepten-6-yl]-5-heptenoic acid, 7-[5-[2-(4-Trifluoromethylphenyl)vinylsulfonylamino]-2-bicyclo[2.2.1]hepten-6-yl]-5-heptenoic acid, 7-[5-[2-(3-Trifluoromethylphenyl)vinylsulfonylamino]-2-bicyclo[2.2.1]hepten-6-yl]-5-heptenoic acid, 7-[5-[2-(2,2-diphenyl)vinylsulfonylamino]-2-bicyclo[2.2.1]hepten-6-yl]-5-heptenoic acid, 7-[3-(2-phenylvinylsulfonylamino)-7-oxabicyclo[2.2.1]heptan-2-yl]-5-heptenoic acid, 7-[3-[2-(4-Fluorophenyl)vinylsulfonylamino]-7-oxabicyclo[2.2.1]heptan-2-yl]-5-heptenoic acid, 7-[3-[2-(3-Fluorophenyl)vinylsulfonylamino]-7-oxabicyclo[2.2.1]heptan-2-yl]-5-heptenoic acid, 7-[3-[2-(4-Chlorophenyl)vinylsulfonylamino]-7-oxabicyclo[2.2.1]heptan-2-yl]-5-heptenoic acid, 7-[3-[2-(3-Chlorophenyl)vinylsulfonylamino]-7-oxabicyclo[2.2.1]heptan-2-yl]-5-heptenoic acid, 7-[3-[2-(4-Bromophenyl)vinylsulfonylamino]-7-oxabicyclo[2.2.1]heptan-2-yl]-5-heptenoic acid, 7-[3-[2-(3-Bromophenyl)vinylsulfonylamino]-7-oxabicyclo[2.2.1]heptan-2-yl]-5-heptenoic acid, 7-[3-[2-(4-Iodophenyl)vinylsulfonylamino]-7-oxabicyclo[2.2.1]heptan-2-yl]-5-heptenoic acid, 7-[3-[2-(3-Iodophenyl)vinylsulfonylamino]-7-oxabicyclo[2.2.1]heptan-2-yl]-5-heptenoic acid, 7-[3-[2-(4-Methylphenyl)vinylsulfonylamino]-7-oxabicyclo[2.2.1]heptan-2-yl]-5-heptenoic acid, 7-[3-[2-(3-Methylphenyl)vinylsulfonylamino]-7-oxabicyclo[2.2.1]heptan-2-yl]-5-heptenoic acid, 7-[3-[2-(4-Nitrophenyl)vinylsulfonylamino]-7-oxabicyclo[2.2.1]heptan-2-yl]-5-heptenoic acid, 7-[3-[2-(3-Nitrophenyl)vinylsulfonylamino]-7-oxabicyclo[2.2.1]heptan-2-yl]-5-heptenoic acid, 7-[3-[2-(4-Methoxyphenyl)vinylsulfonylamino]-7-oxabicyclo[2.2.1]heptan-2-yl]-5-heptenoic acid, 7-[3-[2-(3-Methoxyphenyl)vinylsulfonylamino]-7-oxabicyclo[2.2.1]heptan-2-yl]-5-heptenoic acid, 7-[3-[2-(4-Trifluoromethylphenyl)vinylsulfonylamino]-7-oxabicyclo[2.2.1]heptan-2-yl]-5-heptenoic acid, 7-[3-[2-(3-Trifluoromethylphenyl)vinylsulfonylamino]-7-oxabicyclo[2.2.1]heptan-2-yl]-5-heptenoic acid, 7-[3-[2-(2,2-diphenyl)vinylsulfonylamino]-7-oxabicyclo[2.2.1]heptan-2-yl]-5-heptenoic acid, 7-[2-(2-phenylvinylsulfonylamino)cyclopentyl]-5-heptenoic acid, 7-[2-[2-(4-Fluorophenyl)vinylsulfonylamino]cyclopentyl]-5-heptenoic acid, 7-[2-[2-(3-Fluorophenyl)vinylsulfonylamino]cyclopentyl]-5-heptenoic acid, 7-[2-[2-(4-Chlorophenyl)vinylsulfonylamino]cyclopentyl]-5-heptenoic acid, 7-[2-[2-(3-Chlorophenyl)vinylsulfonylamino]cyclopentyl]-5-heptenoic acid, 7-[2-[2-(4-Bromophenyl)vinylsulfonylamino]cyclopentyl]-5-heptenoic acid, 7-[2-[2-(3-Bromophenyl)vinylsulfonylamino]cyclopentyl]-5-heptenoic acid, 7-[2-[2-(4-Iodophenyl)vinylsulfonylamino]cyclopentyl]-5-heptenoic acid, 7-[2-[2-(3-Iodophenyl)vinylsulfonylamino]cyclopentyl]-5-heptenoic acid, 7-[2-[2-(4-Methylphenyl)vinylsulfonylamino]cyclopentyl]-5-heptenoic acid, 7-[2-[2-(3-Methylphenyl)vinylsulfonylamino]cyclopentyl]-5-heptenoic acid, 7-[2-[2-(4-Nitrophenyl)vinylsulfonylamino]cyclopentyl]-5-heptenoic acid, 7-[2-[2-(3-Nitrophenyl)vinylsulfonylamino]cyclopentyl]-5-heptenoic acid, 7-[2-[2-(4-Methoxyphenyl)vinylsulfonylamino]cyclopentyl]-5-heptenoic acid, 7-[2-[2-(3-Methoxyphenyl)vinylsulfonylamino]cyclopentyl]-5-heptenoic acid, 7-[2-[2-(4-Trifluoromethylphenyl)vinylsulfonylamino]cyclopentyl]-5-heptenoic acid, 7-[2-[2-(3-Trifluoromethylphenyl)vinylsulfonylamino]cyclopentyl]-5-heptenoic acid, 7-[2-[2-(2,2-diphenyl)vinylsulfonylamino]cyclopentyl]-5-heptenoic acid, 6-[6-(2-phenylvinylsulfonylamino)bicyclo[2.2.1]heptan-2-yl]-5-hexenoic acid, 6-[6-[2-(4-Fluorophenyl)vinylsulfonylamino]bicyclo[2.2.1]heptan-2-yl]-5-hexenoic acid, 6-[6-[2-(3-Fluorophenyl)vinylsulfonylamino]bicyclo[2.2.1]heptan-2-yl]-5-hexenoic acid, 6-[6-[2-(4-Chlorophenyl)vinylsulfonylamino]bicyclo[2.2.1]heptan-2-yl]-5-hexenoic acid, 6-[6-[2-(3-Chlorophenyl)vinylsulfonylamino]bicyclo[2.2.1]heptan-2-yl]-5-hexenoic acid, 6-[6-[2-(4-Bromophenyl)vinylsulfonylamino]bicyclo[2.2.1]heptan-2-yl]-5-hexenoic acid, 6-[6-[2-(3-Bromophenyl)vinylsulfonylamino]bicyclo[2.2.1]heptan-2-yl]-5-hexenoic acid, 6-[6-[2-(4-Iodophenyl)vinylsulfonylamino]bicyclo[2.2.1]heptan-2-yl]-5-hexenoic acid, 6-[6-[2-(3-Iodophenyl)vinylsulfonylamino]bicyclo[2.2.1]heptan-2-yl]-5-hexenoic acid, 6-[6-[2-(4-Methylphenyl)vinylsulfonylamino]bicyclo[2.2.1]heptan-2-yl]-5-hexenoic acid, 6-[6-[2-(3-Methylphenyl)vinylsulfonylamino]bicyclo[2.2.1]heptan-2-yl]-5-hexenoic acid, 6-[6-[2-(4-Nitrophenyl)vinylsulfonylamino]bicyclo[2.2.1]heptan-2-yl]-5-hexenoic acid.

6-[6-[2-(3-Nitrophenyl)vinylsulfonylamino]bicyclo[2.2.1]heptan-2-yl]-5-hexenoic acid.

6-[6-[2-(4-Methoxyphenyl)vinylsulfonylamino]bicyclo[2.2.1]heptan-2-yl]-5-hexenoic acid.

6-[6-[2-(3-Methoxyphenyl)vinylsulfonylamino]bicyclo[2.2.1]heptan-2-yl]-5-hexenoic acid, 6-[6-[2-(4-Trifluoromethylphenyl)vinylsulfonylamino]bicyclo[2.2.1]heptan-2-yl]-5-hexenoic acid, 6-[6-[2-(3-Trifluoromethylphenyl)vinylsulfonylamino]bicyclo[2.2.1]heptan-2-yl]-5-hexenoic acid, 6-[6-[2-(2,2-diphenyl)vinylsulfonylamino]bicyclo[2.2.1]heptan-2-yl]-5-hexenoic acid, 6-[6-(2-phenylvinylsulfonylamino)bicyclo[2.2.2]octan-2-yl]-5-hexenoic acid, 6-[6-[2-(4-Fluorophenyl)vinylsulfonylamino]bicyclo[2.2.2]octan-2-yl]-5-hexenoic acid, 6-[6-[2-(3-Fluorophenyl)vinylsulfonylamino]bicyclo[2.2.2]octan-2-yl]-5-hexenoic acid, 6-[6-[2-(4-Chlorophenyl)vinylsulfonylamino]bicyclo[2.2.2]octan-2-yl]-5-hexenoic acid, 6-[6-[2-(3-Chlorophenyl)vinylsulfonylamino]bicyclo[2.2.2]octan-2-yl]-5-hexenoic acid, 6-[6-[2-(4-Bromophenyl)vinylsulfonylamino]bicyclo[2.2.2]octan-2-yl]-5-hexenoic acid, 6-[6-[2-(3-Bromophenyl)vinylsulfonylamino]bicyclo[2.2.2]octan-2-yl]-5-hexenoic acid, 6-[6-[2-(4-Iodophenyl)vinylsulfonylamino]bicyclo[2.2.2]octan-2-yl]-5-hexenoic acid, 6-[6-[2-(3-Iodophenyl)vinylsulfonylamino]bicyclo[2.2.2]octan-2-yl]-5-hexenoic acid, 6-[6-[2-(4-Methylphenyl)vinylsulfonylamino]bicyclo[2.2.2]octan-2-yl]-5-hexenoic acid, 6-[6-[2-(3-Methylphenyl)vinylsulfonylamino]bicyclo[2.2.2]octan-2-yl]-5-hexenoic acid, 6-[6-[2-(4-Nitrophenyl)vinylsulfonylamino]bicyclo[2.2.2]octan-2-yl]-5-hexenoic acid, 6-[6-[2-(3-Nitrophenyl)vinylsulfonylamino]bicyclo[2.2.2]octan-2-yl]-5-hexenoic acid, 6-[6-[2-(4-Methoxyphenyl)vinylsulfonylamino]bicyclo[2.2.2]octan-2-yl]-5-hexenoic acid, 6-[6-[2-(4-Trifluoromethylphenyl)vinylsulfonylamino]bicyclo[2.2.2]octan-2-yl]-5-hexenoic acid, 6-[6-[2-(3-Trifluoromethylphenyl)vinylsulfonylamino]bicyclo[2.2.2]octan-2-yl]-5-hexenoic acid, 6-[6-[2-(2,2-diphenyl)vinylsulfonylamino]bicyclo[2.2.2]octan-2-yl]-5-hexenoic acid, and ester, amido, amido with amino acid thereof.

The ester compounds, amide compounds and amide compounds with amino acid, themselves, have only week pharmacological activites, but they show strong activities when an ester and amide bonds thereof are broken in the body after administration of them. They are what is called a prodrug.

Cyclodextrin Clathrates

The cyclodextrin clathrates of the compounds of the formula (Ix) and (Iy) of the present invention may be prepared by the method described in the specification of the British Patent No. 1351238 or the British Patent No. 1419221, using α, β or γ-cyclodextrins or a mixture thereof.

By converting into cyclodextrin clathrates, the stability of the compounds of the formula (Ix) and (Iy) can be increased.

Salts

The compounds which $R^{11}$ is hydrogen or $NR^{13}R^{14}$ is amino acid residue among the compounds of the formula (Ix), or $R^{200}$ is hydroxy or $NR^{230}R^{240}$ is amino acid residue among the compounds of the formula (Iy), of the present invention may be converted into the corresponding salts. Non-toxic and water-soluble salts are preferable. Suitable salts, for example, are follows:

salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

Process for the Preparation

1) The compounds of the formula (Ix) are disclosed in the specification of the U.S. Pat. No. 5,168,101 and the U.S. Pat. No. 4,861,913, and the detailed processes for the preparation thereof are also disclosed therein.

The structures of unspecified compounds are described with physical data in example described hereafter in the present specification.

The compounds in which $R^{3a}$ is benzene, naphthalene or C4-7 cycloalkyl substituted by trifluoromethyl, and in which $R^{2b}$ or $R^{2c}$ is C1-4 alkoxy, hydroxy, cyano, nitro or trifluoromethyl, in the compounds of the formula (Ix), may be also prepared by the same method as mentioned above.

2) The compounds of the formula (Iy) may be prepared as follows.

The compounds wherein $R^{200}$ is $R^{201}$ in which $R^{201}$ is C1-20 alkoxy or $NR^{230}R^{240}$ (wherein all the symbols are the same meaning as hereinbefore defined), in the compounds of the formula (Iy), of the formula:

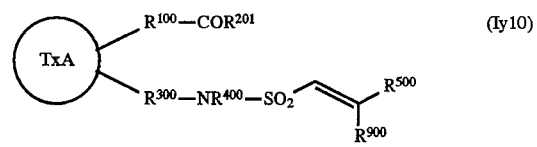

wherein all the symbols are the same meaning as hereinbefore defined, may be prepared from those of the formula:

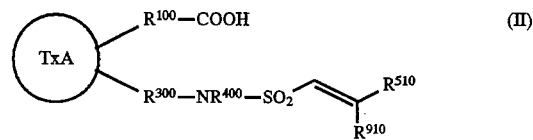

wherein $R^{510}$ and $R^{910}$ each, independently, is

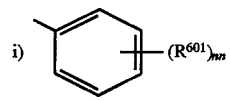

in which $R^{601}$ is hydrogen, C1–4 alkyl, C1–4 alkoxy, halogen, trifluoromethyl, nitro or 2-tetrahydropyranyloxy;

nn is the same meaning as hereinbefore defined;

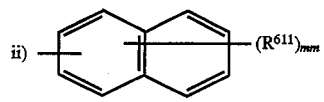

in which $R^{611}$ is hydrogen, C1–4 alkyl, C1–4 alkoxy, halogen, trifluoromethyl, nitro or 2-tetrahydropyranyloxy;

mm is the same meaning as hereinbefore defined;

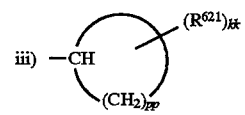

in which $R^{621}$ is hydrogen, C1–4 alkyl, C1–4 alkoxy, halogen, trifluoromethyl, nitro or 2-tetrahydropyranyloxy;

kk and pp are the same meaning as hereinbefore defined;

iv) C1–7 alkyl or v) hydrogen, and the other symbols are the same meaning as hereinbefore defined; by the esterification reaction or the reaction of forming amide-bond, and by the hydrolysis in an acidic condition when $R^{601}$, $R^{611}$ and $R^{621}$ is 2-tetrahydropyranyloxy.

The esterification reaction is known, for example, it may be carried out using (i) diazoalkane, (ii) a condensing agent (e.g. dicyclohexylcarbodiimide, Mukaiyama reagent etc.)

The method using diazoalkane of (i) is known, for example, it may be carried out using the corresponding diazoalkane, in an inert organic solvent (e.g. tetrahydrofuran (THF), dioxan, ether, acetone etc.) at −10° C.~−40° C.

The method using a esterification agent of (ii) is known, for example, it may be carried out in an corresponding alkanol, using a condensing agent (dicyclohexylcarbodiimide, Mukaiyama reagent etc.) and tertiary amine (e.g. triethylamine etc.) at −10° C.~40° C.

The reaction to forming amide-bond is known, for example, it may be carried out (i) with using a corresponding amine of the formula $HNR^{230}R^{240}$ wherein $R^{230}$ and $R^{240}$ are the same meaning as hereinbefore defined, in an inert organic solvent (e.g. methylene chloride, toluene etc.) at 0° C.~−40° C., after reacting oxalyl chloride, or (ii) with using a corresponding amine, Mukaiyama reagent and tertiary amine (e.g. triethylamine etc.), in an inert organic solvent (e.g. methylene chloride etc.), at 0° C.~−40° C. In case that an amine of the formula $HNR^{230}R^{240}$ is amino acid, the reaction is carried out by reacting the compounds in which carboxyl in an amino acid is protected by appropriate alkyl, or the compounds in which an amino having no connection to the reaction is protected by tert-butoxycarbonyl (boc) or benzyloxy carbonyl (cbz), and then hydrolyzing with using an acid (trifuruoroacetic acid etc.) or an alkali (sodium hydroxide etc.) to remove a protecting group.

The hydrolysis of ester in an acidic condition is known, for example, it may be carried out in water-miscible organic solvent (e.g. methanol, ethanol, THF, dioxan etc.), using an organic acid (e.g. acetic acid, p-toluenesulfonic acid, trichloroacetic acid etc.) or an inorganic acid (e.g. hydrochloride, sulfate, hydrobromide etc.) at 0° C.~−90° C.

The compounds which $R^{200}$ is hydroxy in the compounds of the formula (Iy), of the formula:

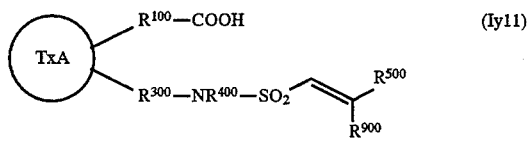

wherein all the symbols are the same meaning as hereinbefore defined;
may be prepared from those of the formula:

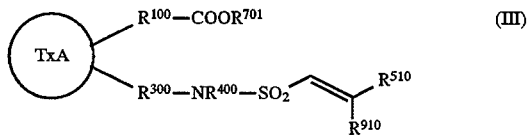

wherein $R^{701}$ is C1–4 alkyl and the other symbols are the same meaning as hereinbefore defined;

by the hydrolysis in an alkaline condition, and by the hydrolysis in an acidic condition when $R^{601}$, $R^{611}$ and $R^{621}$ is 2-tetrahydropyranyloxy.

The hydrolysis of ester in an alkaline condition is known, for example, it may be carried out in a water-miscible organic solvent (e.g. THF, methanol, ethanol dimethoxyethane or mixture thereof etc.), using an alkali (e.g. sodium hydroxide, potassium hydroxide etc.), at −10° C.~−100° C.

The hydrolysis of ester in an acidic condition may be carried out the same procedure as mentioned above.

Besides, the procedure of this two reactions may be carried out reversibly.

The compounds of the formula (II) may be prepared from those of the formula (III) by the hydrolysis in an alkaline condition.

The hydrolysis of ester in an alkaline condition may be carried out the same procedure as mentioned above.

The compounds of the formula (III) may be prepared by using a reaction depicted in following Scheme (A).

The reaction step in parenthesis may be carried out, if desired.

The symbols in scheme is the following meaning or the same meaning as hereinbefore defined.

| | |
|---|---|
| THP: | 2-tetrahydropyranyl, |
| $R^{101}$: | a single bond or C1–4 alkylene, |
| $R^{102}$: | C1–5 alkylene, |
| $R^{810}$: | t-butoxycarbonyl, |
| $R^{401}$: | C1–4 alkyl, |
| $X^{10}$: | halogen, |
| $X^{20}$: | halogen, |
| $X^{30}$: | halogen, |
| $X^{40}$: | halogen, |
| $\phi$: | phenyl |
| TsOH: | p-toluenesulfonic acid |

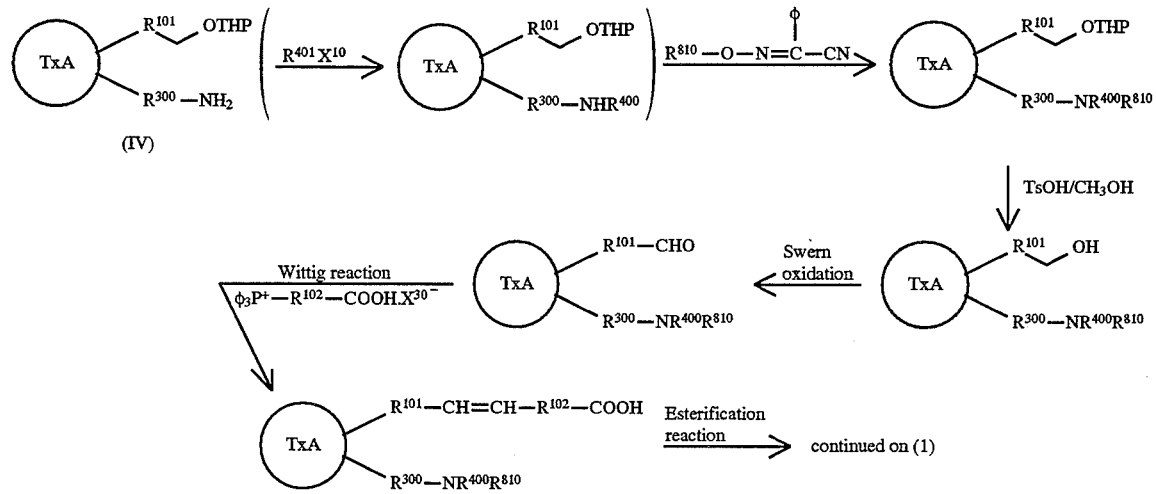

-continued
Scheme (A)

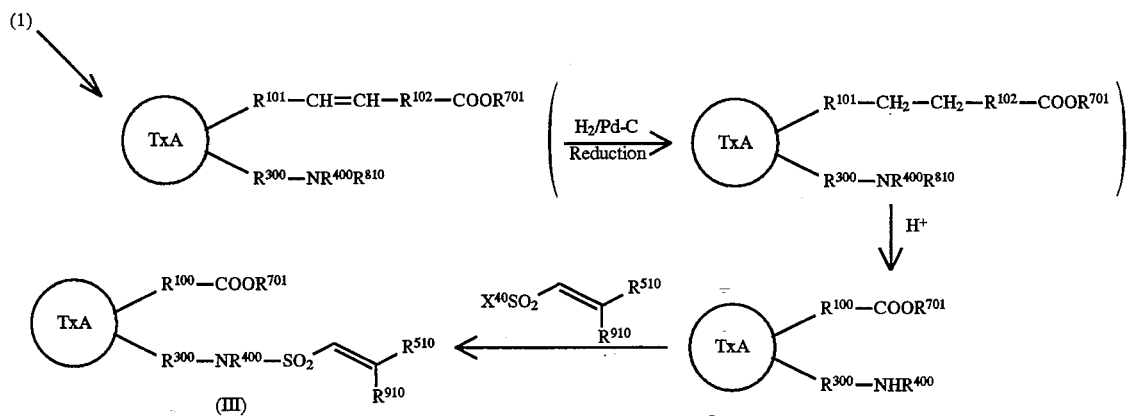

In the formula (Iy), the compounds in which $R^{100}$ is C4–7 alkenylene, $R^{200}$ is hydroxy, $R^{500}$ is $R^{501}$, wherein $R^{501}$ is i) 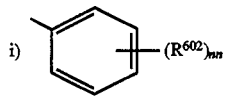

in which $R^{602}$ is hydrogen, C1–4 alkyl, C1–4 alkoxy, halogen, trifluoromethyl or nitro, nn is the same meaning as hereinbefore defined, or ii) 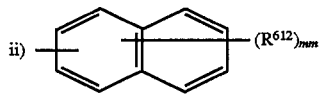

in which $R^{612}$ is hydrogen, C1–4 alkyl, C1–4 alkoxy, halogen, trifluoromethyl or nitro, mm is the same meaning as hereinbefore defined, or iii) 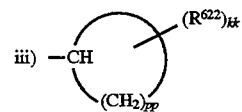

in which $R^{622}$ is hydrogen, C1–4 alkyl, C1–4 alkoxy, halogen, trifluoromethyl or nitro, kk and pp are the same meaning as hereinbefore defined, or
iv) C1–7 alkyl and $R^{900}$ is hydrogen;
of the formula:

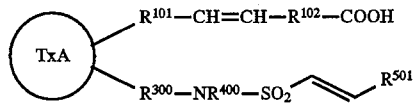 (Iy12)

wherein all the symbols are the same meaning as hereinbefore defined;

may be prepared by subjecting the compound of the formula:

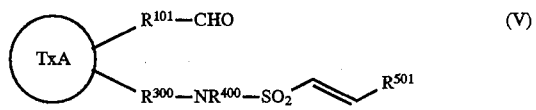 (V)

wherein all the symbols are the same meaning as hereinbefore defined; and the compound of the formula:

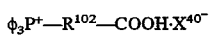 (VI)

wherein $X^{40}$ is halogen, $\phi$ is phenyl, $R^{102}$ is the same meaning as hereinbefore defined;
to wittig reaction.

Wittig reaction is known, for example, it may be carried out by reacting the phosphonium salt mentioned above in an inert organic solvent (e.g. toluene, THF, dimethylsulfoxide (DMSO) etc.), in the presence of a strong base (e.g. potassium tert-butoxide, lithium diisopropylamide, sodium hydroxide etc.), at −78° C. to room temperature.

The compounds of the formula (V) may be prepared by using a reaction depicted in following Scheme (B).

The reaction step in parenthesis may be carded out, it desired.

The symbols in scheme is the following meaning or the same meaning as hereinbefore defined.

| $X^{50}$: | halogen, |
|---|---|
| Me: | methyl, |
| Et$_3$N: | triethylamine, |
| n-BuLi: | n-butyl lithium |

Scheme (B)

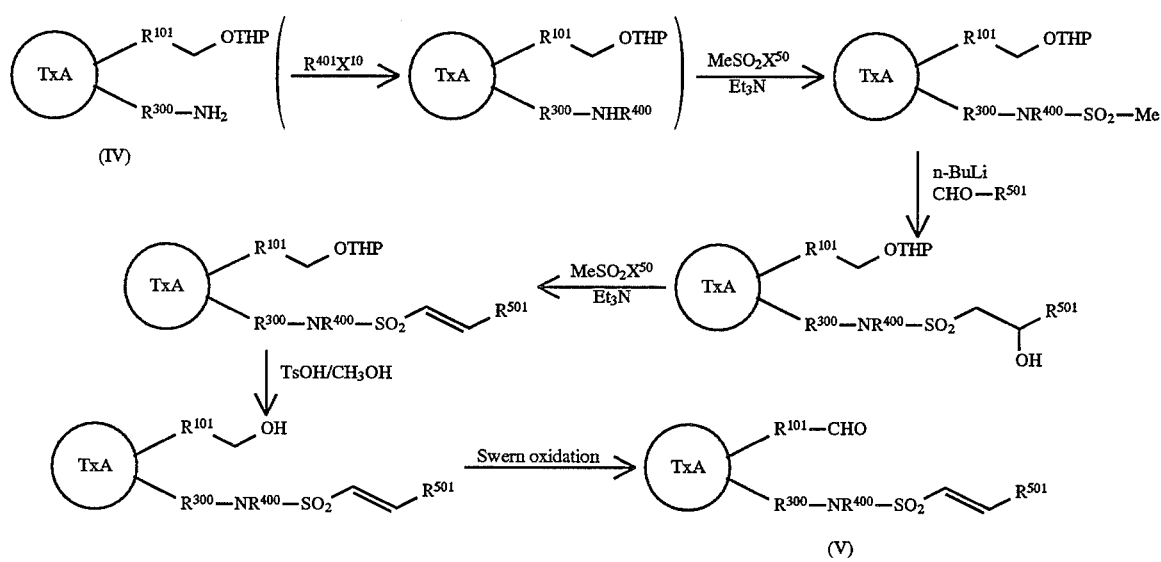

As mentioned above, the compounds of the present invention contain various optical isomers due to asymmetric carbon(s) thereof. However, when a single or a specific optically active substance is desired, it may be prepared by using a compound having the desired optical activity as a starting material, or by resolving into each optically active substance at a preferable step by means such as optical resolution etc.

Starting Materials and Reagents

The starting materials and reagents in the present invention are known per se or may be prepared by known methods.

For example, the compound which

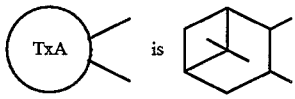

in the compounds of the formula (IV) is described in specification of the U.S. Pat. No. 4,861,913 and the U.S. Pat. No. 5,168,101.

Pharmacological Activities

The compounds of the present invention of the formula (Ix) and (Iy) are useful for $PGE_2$ antagonists or agonists, because they bind onto prostaglandin $E_2$ receptor and have an activity of antagonist or agonist against the action thereof. $PGE_2$ antagonists are expected to inhibit an uterine contraction, to have an analgetic action, to inhibit digestive peristalsis, to induce sleep. $PGE_2$ agonists are expected to have uterine contractile activity, to promote digestive peristalsis, to suppress gastric acid secretion, to lower blood pressure.

For example, in standard laboratory test, the effects were confirmed by (i) the Inhibitory effects of $[^3H]$-$PGE_2$ receptor binding in rat uterus membrane fraction, (ii) the inhibitory effects of rat uterine contraction induced by $PGE_2$.

The results of the experiments are shown in the table I and table II.

(i) The measurement of the inhibition of $[^3H]$-$PGE_2$ receptor binding

The standard assay mixture contained 5 nM $[^3H]$-$PGE_2$ (50 µl), test compounds (50 µl) and crude membrane fraction obtained from rat uterus (1.2 mg protein/ml, 100 µl) in a final volume of 200 µl (10 mM potassium phosphate pH 6.0, 0.1M NaCl (buffer A)). After incubation for 1 hour at room temperature, the reaction was stopped by the addition of 3 ml of ice-cold buffer A, after which the mixture was rapidly filtered through a Whatman GF/B glass filter. The radioactivity associated with the filter was measured in ACS II (Amarsham) by liquid scintillation counting. Percent inhibition of specific $[^3H]$-$PGE_2$ binding or $IC_{50}$ value, the concentration required to compete with $^3H$-$PGE_2$ receptor binding by 50% were calculated.

TABLE I

Inhibitory effects of $PGE_2$ receptor binding in rat

| Structure | Ex. No. | $IC_{50}$ (µM) |
|---|---|---|
| (phenyl) | 3 (m) | 0.0054 |
| (H) | 3 (n) | 0.12 |
| (Et-phenyl) | 3 (b) | 0.57 |

TABLE I-continued

Inhibitory effects of PGE$_2$ receptor binding in rat

| Structure | Ex. No. | IC$_{50}$ (μM) |
|---|---|---|
| (bicyclic)-CH=CH-CH$_2$-COOH; NHSO$_2$-C$_6$H$_4$-tBu | 3 (c) | 6.3 |
| (bicyclic)-CH=CH-CH$_2$-COOH; NHSO$_2$-alkyl | 3 (j) | 5.0 |
| (bicyclic)-CH=CH-CH$_2$-COOH; NHSO$_2$-C$_6$H$_4$-F | 3 (e) | 2.6 |
| (bicyclic)-CH=CH-CH$_2$-COOH; NHSO$_2$-C$_6$H$_4$-Cl | 3 (f) | 0.75 |
| (bicyclic)-CH=CH-CH$_2$-COOH; NHSO$_2$-C$_6$H$_4$-Br | 2 | 0.44 |
| (bicyclic)-CH=CH-CH$_2$-COOH; NHSO$_2$-C$_6$H$_4$-OMe | 3 (d) | 0.82 |
| (bicyclic)-CH=CH-CH$_2$-COOH; NHSO$_2$-C$_6$H$_5$ | 3 (a) | 7.6 |
| (bicyclic)-CH=CH-CH$_2$-COOH; NHSO$_2$-alkyl | 3 (k) | 0.025 |
| (bicyclic)-CH=CH-CH$_2$-COOH; NHSO$_2$-alkyl | 3 (l) | 0.36 |
| (bicyclic)-CH=CH-CH$_2$-COOH; NHSO$_2$-naphthyl | 3 (i) | 0.09 |
| (bicyclic)-CH=CH-CH$_2$-COOH; NHSO$_2$-C$_6$H$_4$-NO$_2$ | 3 (h) | 0.21 |
| (bicyclic)-CH=CH-CH$_2$-COOH; NHSO$_2$-C$_6$H$_4$-I | 3 (g) | 0.054 |
| (±) (bicyclic)-CH=CH-CH$_2$-COOH; NHSO$_2$-C$_6$H$_4$-Me | 5 (b) | 3.4 |
| (bicyclic)-CH=CH-CH$_2$-COOH; NHSO$_2$-C$_6$H$_4$-Me | 4 | 3.4 |
| (±) (bicyclic)-CH=CH-CH$_2$-COOH; NHSO$_2$-C$_6$H$_4$-Me | 5 (c) | 5.7 |
| (±) (bicyclic)-CH=CH-CH$_2$-COOH; CH$_2$NHSO$_2$-C$_6$H$_4$-Me | U.S. Pat. No. 5168101 1 (p) | 6.4 |
| (bicyclic)-CH=CH-CH$_2$-COOH; CH$_2$NHSO$_2$-C$_6$H$_4$-Me | U.S. Pat. No. 5168101 1 (x) | 1.6 |
| (bicyclic)-CH=CH-CH$_2$-COOH; CH$_2$NHSO$_2$-C$_6$H$_4$-Br | U.S. Pat. No. 5168101 1 (y) | 0.62 |
| (bicyclic)-CH=CH-CH$_2$-COOH; CH$_2$NHSO$_2$-C$_6$H$_4$-Br | U.S. Pat. No. 5168101 1 (cc) | 0.39 |

TABLE I-continued
Inhibitory effects of PGE$_2$ receptor binding in rat
| Structure | Ex. No. | IC$_{50}$ (μM) |
|---|---|---|
| 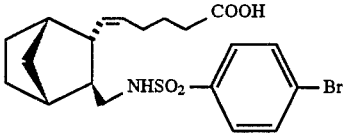 | 5 (i) | 6.5 |
| 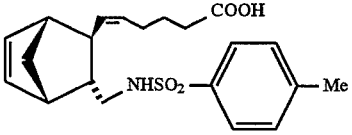 | U.S. Pat. No. 5168101 1 (aa) | 2.0 |
| 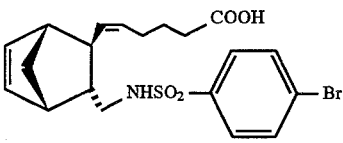 | U.S. Pat. No. 5168101 1 (bb) | 0.82 |
| 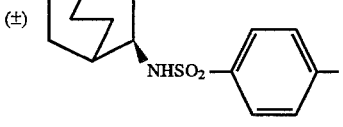 (±) | 5 (a) | 3.6 |
| 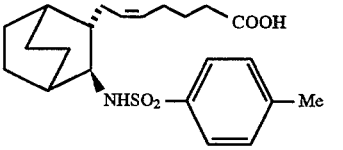 | 5 (d) | 2.1 |
| 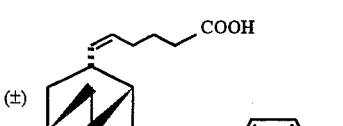 (±) | U.S. Pat. No. 5168101 1 (a) | 0.77 |
| 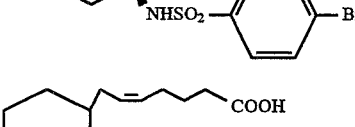 more polar | 5 (e) | 0.06 |
| 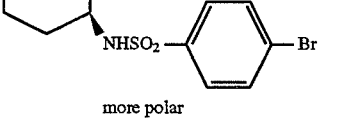 (±) less polar | 5 (f) | 5.0 |
| 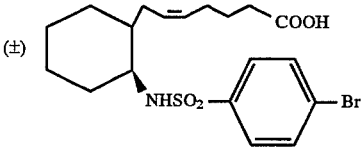 | U.S. Pat. No. 5168101 1 (t) | 1.2 |
| 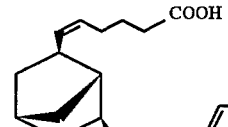 (±) | U.S. Pat. No. 5168101 1 (b) | 3.5 |
| 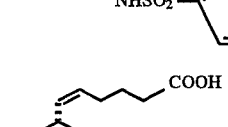 (±) | U.S. Pat. No. 5168101 1 (c) | 0.5 |
| 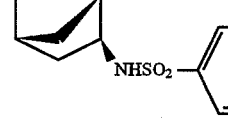 (±) | U.S. Pat. No. 5168101 1 (l) | 2.4 |
| 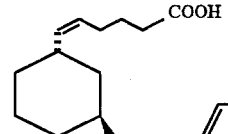 (±) | U.S. Pat. No. 5168101 1 (m) | 0.5 |
| 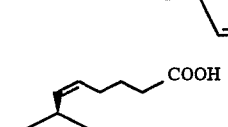 (±) | 5 (g) | 3.5 |
| 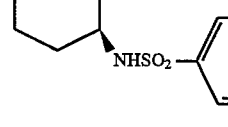 (±) | 5 (h) | 0.2 |
| 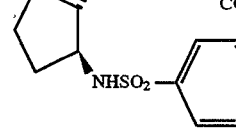 (±) | European Patent Publication No. 0312906 1 (v) | 1.8 |
| 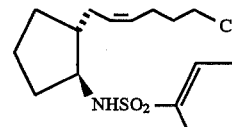 (±) | European Patent Publication No. 0312906 1 (w) | 8.0 |

TABLE I-continued

Inhibitory effects of PGE$_2$ receptor binding in rat

| Structure | Ex. No. | IC$_{50}$ (μM) |
|---|---|---|
| [structure: cyclopentane with COOH chain and NHSO$_2$-C$_6$H$_4$-Br] | U.S. Pat. No. 5168101 1 (i) | 2.4 |

TABLE II

Inhibitory effects of PGE$_2$ receptor binding in rat

| Structure | Ex. No. | IC$_{50}$ (μM) |
|---|---|---|
| [bicyclic structure with COOH chain and NHSO$_2$-CH=CH-C$_6$H$_4$-F] | 6 (2) | 0.0036 |
| [bicyclic structure with COOH chain and NHSO$_2$-CH=CH-alkyl] | 6 (14) | 0.8 |
| [bicyclic structure with COOH chain and NHSO$_2$-CH=CH-C$_6$H$_5$] | 6 (12) | <0.01 |
| [norbornane structure with COOH chain and NHSO$_2$-CH=CH-C$_6$H$_5$] | 6 (18) | 0.017 |
| (±) [cyclohexane with COOH chain and NHSO$_2$-CH=CH-C$_6$H$_5$] | 6 (19) | 0.23 |
| (±) [cyclohexane with COOH chain and NHSO$_2$-CH=CH-C$_6$H$_5$] | 6 (21) | 0.6 |
| [cyclopentane with COOH chain and NHSO$_2$-CH=CH-C$_6$H$_5$] | 6 (22) | 1.8 |

TABLE II-continued

Inhibitory effects of PGE$_2$ receptor binding in rat

| Structure | Ex. No. | IC$_{50}$ (μM) |
|---|---|---|
| [structure with NHSO$_2$, COOH, phenyl] | 6 (26) | 0.038 |
| [structure with NHSO$_2$, COOH, two phenyls] | 9 | 0.26 |

(ii) The inhibitory effects of compounds on contraction of rat uterus induced by PGE$_2$ Pseudo pregnant rat uterus (Sprague Dawley, 200–300 g, induced by oestradiol 500 μl/kg s.c. 18–24 hours before experiment) was isolated and longitudinal strips of 1–1.5 cm were set up in Locke-Ringer solution containing low Ca$^{2+}$, aerated with mixed gas (oxygen 95%+carbon dioxide 5%) at 28° C. A resting tension of 1 g was imposed on the tissue and contraction were recorded isometrically and displayed on recticorder.

The compound of example 6(12) completely inhibited the contraction induced by 0.3 μM PGE$_2$.

Toxicity

The toxicity of the compound of the present invention of the formula (Ix) and (Iy) are very low and therefore, it may be estimated safe for pharmaceutical use.

For example, the acute toxicity (LD$_{50}$) in mouse of 6-[(1S, 2R, 3R, 4R)-3-(4-bromophenylsulfonyl-aminomethyl)bicyclo[2.2.1]heptan-2-yl]-5Z-hexenoic acid (it is described as example 1(y) in specification of the U.S. Pat. No. 5,168,101.) was more than 300 mg/kg by oral administration.

Application for Pharmaceuticals

The compounds of the present invention of the formula (Ix) and (Iy), cyclodextrin clathrates thereof and non-toxic salts thereof, are useful for PGE$_2$ antagonists or agonists, because they bind onto prostaglandin E$_2$ receptor and have an activity of antagonist or agonist against the action thereof.

PGE$_2$ antagonists are considered to inhibit uterine contraction, to have an analgetic action, to inhibit digestive peristalsis, to induce sleep, therefor they are useful for prevention and/or treatment of abortion, pain, diarrhea, insomnia.

PGE$_2$ agonists are considered to have uterine contractile activity, to promote digestive peristalsis, to suppress gastric acid secretion, to lower blood pressure, therefor they are useful for prevention and/or treatment of constipation, ulcer, gastritis, hypertensive, and for induction of labour in pregnant female mammals.

For the purpose above described, the compounds of the formula (Ix) and (Iy), of the present invention and cyclodextrin clathrates thereof and non-toxic salts thereof may be normally by administered systemically or partially usually by oral or parenteral administration.

The doses to be administered is determined depending upon age, body weight, symptom, the desired therapeutic effect, the route of administration, and the duration of the treatment etc. In the human adult, the doses per person per dose are generally between 0.01 mg and 0.1 mg, by oral administration up to several times per day, and between 1 μg and 100 μg, by parenteral administration up to several times per day. As mentioned above, the doses to be used depend upon various conditions. Therefore, there are cases in which doses lower than or greater than the ranges specified above may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium glycolate, stabilizing agent e.g. lactose and assistant for dissolving e.g. arginine, glutamic acid or aspartic acid. The tablets or pills may, if desired, be made into gastric film-coated or enteric film-coated tablets or pills, such as sugar-coated, gelatin-coated, hydroxypropyl cellulose-coated or hydroxypropylmethyl cellulose phthalate-coated tablets or pills; two or more of layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ethanol, POLYSORBATE 80 (registered Trade Mark). These compositions may also include adjuvants such as preserving, wetting, emulsifying, dispersing agents, stabilizing agents (e.g. lactose) and assistant agent for dissolving (e.g. arginine, glutamic acid or aspartic acid). They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

REFERENCE EXAMPLES AND EXAMPLES

The following reference examples and examples illustrate the present invention, but not limit the present invention.

In the reference examples and examples, "TLC", "NMR", "IR" and "MS" represent "Thin layer chromatography", "Nuclear magnetic resonance spectrum", "Infrared absorption spectrum" and "Mass spectrum", respectively.

The solvents in the parentheses show the developing or eluting solvents and the rations of the solvents used are by volume in chromatographic separations.

Unless otherwise specified, "NMR" was measured in a chloroform-d (CDCl$_3$) solution and "IR" was measured by the liquid film method respectively.

And (±) in reference examples and examples represent the mixture of enantiomers having different angles of rotation as generally used in the nomenclature. For example,

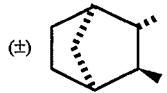

represents the mixture of

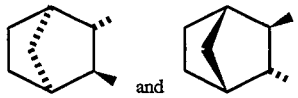

and * are added to indications of absolute configuration at the same time.

Example 1

7-[(1S,2S,3S,5R)-3-(4-bromophenyl)sulfonylamino-6,6-dimethylbicyclo [3.1.1]heptan-2-yl]-5Z-heptenoic acid methyl ester

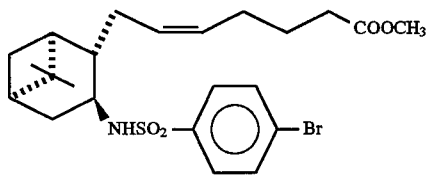

A solution of 7-[(1S,2S,3S,5R)-3-amino-6,6-dimethylbicyclo[3.1.1]heptan-2-yl]-5Z-heptenoic acid methyl ester (the compound was described as reference example 14 in specification of the U.S. Pat. No. 4,792,550.) (140 mg) in pyridine (5 ml) was cooled with ice-bath. A solution of 4-bromobenzenesulfonyl chloride (153 mg) in methylene chloride (2 ml) was dropped to the above solution. The mixture was stirred for 16 hours at room temperature. The reaction mixture was poured into 4N hydrochloric acid (30 ml) and extracted with ethyl acetate. The extract was washed with saturated sodium bicarbonate and brine, successively, dried over magnesium sulfate and concentrated under reduced pressure. The residue was purified by column chromatography on silica gel (ethyl acetate: n-hexane=1:6) to give the title compound (155 mg) having the following physical data.

NMR: δ 7.77 (2H, d), 7.64 (2H, d), 5.29 (2H, m), 4.62 (2H, d), 3.70 (3H, s), 3.59 (1H, m), 2.30 (2H, t), 1.18 (3H, s), 0.95 (3H, s), 0.76 (1H, d);

MS: m/e 497 (M$^+$), 499, 466, 468, 428, 430, 401, 403, 396, 398.

Example 2

7-[(1S,2S,3S,5R)-3-(4-bromophenyl)sulfonylamino-6,6-dimethylbicyclo [3.1.1]heptan-2-yl]-5Z-heptenoic acid

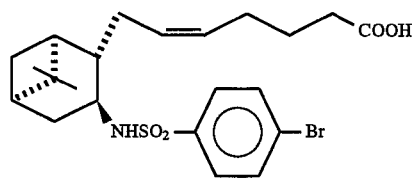

To a solution of the methyl ester compound prepared in example 1 (60 mg) in methanol (6 ml), 10% sodium hydride solution (2 ml) was added. The mixture was stirred for 5 hours at room temperature. After methanol was distilled off from the reaction mixture, ice and 3N hydrochloric acid (20 ml) were added to the residue. The above solution was extracted with ethyl acetate (three times). The extract was dried over magnesium sulfate and concentrated under reduced pressure to give the title compound (53 mg) having the following physical data.

TLC: Rf 0.45 (methylene chloride: methanol=10:1);

NMR: δ 7.77 (2H, td), 7.65 (2H, td), 5.50~5.24 (3H, m), 3.63 (1H, m), 2.43~1.42 (14H), 1.17 (3H, s), 0.94 (3H, s), 0.76 (1H, d);

MS: m/e 483 (M$^+$), 465, 414, 396;

Feature: pale yellow amorphous.

Example 3

By the same procedure as in example 1→example 2, using 7-[(1S,2S,3S,5R)-3-amino-6,6-dimethylbicyclo [3.1.1]heptan-2-yl]-5Z-heptenoic acid methyl ester (the compound was described as reference example 14 in specification of the U.S. Pat. No. 4,792,550.) and various sulfonyl compounds as starting material, purposed compounds shown in following table were given.

TABLE III

[Structure: bicyclo[3.1.1]heptane with NHSO2—R²—R³ substituent and 5Z-heptenoic acid (COOH) chain]

| Example No. | —R²—R³ | Name | TLC (Rf) | NMR (δ) | MS (m/e) | Feature |
|---|---|---|---|---|---|---|
| 3 (a) | [phenyl] | 7-[(1S,2S,3S,5R)-3-phenyl sulfonylamino-6,6-dimethyl bicyclo[3.1.1]heptan-2-yl]-5Z-heptenoic acid | 0.50 (methylene chloride: methanol = 10:1) | 7.92(2H, m), 7.55(3H,m), 5.34(3H, m), 3.66(1H,m), 2.40–1.44(14H), 1.16(3H, s), 0.94(3H, s), 0.79(1H, d) | 405(M⁺), 387,336, 318 | pale yellow wax |
| 3 (b) | [phenyl]—C₂H₅ | 7-[(1S,2S,3S,5R)-3-(4-ethylphenyl)sulfonylamino-6, 6-dimethylbicyclo[3.1.1]heptan-2-yl]-5Z-heptenoic acid | 0.50 (methylene chloride: methanol = 10:1) | 7.80(2H, d), 7.31(2H, d), 5.35(2H, m), 5.16(1H, d), 3.62(1H, m), 2.71(2H, q), 2.35(2H, t), 2.30–1.40(13H, m), 1.24(3H, t), 1.16(3H, s), 0.94(3H, s), 0.76(1H, d) | 433(M⁺), 415, 364, 346, 337, 238, 237 | pale yellow oil |
| 3 (c) | [phenyl]—C(CH₃)₃ | 7-[(1S,2S,3S,5R)-3-(4-tert-butylphenyl)sulfonylamino-6, 6-dimethylbicyclo[3.1.1]heptan-2-yl]-5Z-heptenoic acid | 0.50 (methylene chloride: methanol = 10:1) | 7.80(2H, dt), 7.48(2H, dt), 5.32(2H, m), 5.12(1H, broad), 3.63(1H, broad), 2.35(2H, t), 2.30–1.40(13H), 1.34(9H, s), 1.16(3H, s), 0.94(3H, s), 0.76(1H, d) | 461(M⁺), 443, 392, 374, 365, 294 | pale yellow wax |
| 3 (d) | [phenyl]—OCH₃ | 7-[(1S,2S,3S,5R)-3-(4-methoxy phenyl)sulfonylamino-6, 6-dimethylbicyclo[3.1.1]heptan-2-yl]-5Z-heptenoic acid | 0.50 (mehylene chloride: methanol = 10:1) | 7.82(2H, dt), 6.96(2H, dt), 5.38(2H, m), 5.00(1H, broad), 3.85(3H, s), 3.58(1H, m), 2.40–1.40(14H), 1.16(3H, s), 0.93(3H, s), 0.76(1H, d) | 435(M⁺), 417, 366, 348, 339 | colorless wax |
| 3 (e) | [phenyl]—F | 7-[(1S,2S,3S,5R)-3-(4-fluoro phenyl)sulfonylamino-6, 6-dimethylbicyclo[3.1.1]heptan-2-yl]-5Z-heptenoic acid | 0.45 (mehylene chloride: methanol = 10:1) | 7.92(2H, dd), 7.18(2H, t), 5.38(3H, m), 3.62(1H, broad), 2.42–1.40(14H), 1.18(3H, s), 0.95(3H, s), 0.76(1H, d) | 423(M⁺), 405, 354, 336 | colorless wax |
| 3 (f) | [phenyl]—Cl | 7-[(1S,2S,3S,5R)-3-(4-chloro phenyl)sulfonylamino-6, 6-dimethylbicyclo[3.1.1]heptan-2-yl]-5Z-heptenoic acid | 0.45 (mehylene chloride: methanol = 10:1) | 7.84(2H, dt), 7.48(2H, dt), 5.40(3H, m), 3.62(1H, broad), 2.42–1.40(14H), 1.18(3H, s), 0.95(3H, s), 0.76(1H, d) | 439(M⁺), 421, 398, 370, 352, 272 | pale yellow wax |
| 3 (g) | [phenyl]—I | 7-[(1S,2S,3S,5R)-3-(4-iodophenyl)sulfonylamino-6, 6-dimethylbicyclo[3.1.1]heptan-2-yl]-5Z-heptenoic acid | 0.45 (methylene cloride: methanol = 10:1) | 7.85(2H, dt), 7.60(2H, dt), 5.35(2H, m), 5.23(1H, d), 3.61(1H, m), 2.40–1.40(14H), 1.16(3H, s), 0.93(3H, s), 0.76(1H, d) | 531(M⁺), 513, 463, 444, 425 | white solid |
| 3 (h) | [phenyl]—NO₂ | 7-[(1S,2S,3S,5R)-3-(4-nitrophenyl)sulfonylamino-6, 6-dimethylbicyclo[3.1.1]heptan-2-yl]-5Z-heptenoic acid | 0.40 (methylene cloride: methanol = 10:1) | 8.34(2H, dt), 8.08(2H, dt), 5.49(1H, d), 5.36(2H, m), 3.79(1H, m), 2.40–1.40(14H), 1.08(3H, s), 0.94(3H, s), 0.76(1H, d) | 450(M⁺), 432, 331, 363 | white wax |
| 3 (i) | [2-naphthyl] | 7-[(1S,2S,3S,5R)-3-(2-naphtyl)sulfonylamino-6, 6-dimethylbicyclo[3.1.1]heptan-2-yl]-5Z-heptenoic acid | 0.55 (methylene cloride: methanol = 10:1) | 8.46(1H, d), 7.92(4H, m), 7.62(2H, m), 5.30(3H, m), 3.68(1H, m), 2.40–1.44(14H), 1.14(3H, s), 0.92(3H, s), 0.78(1H, d) | 455(M⁺), 437, 414, 386, 368, 359 | white solid |
| 3 (j) | —(CH₂)₃CH₃ | 7-[(1S,2S,3S,5R)-3-butyl sulfonylamino-6, 6-dimethyl bicyclo[3.1.1]heptan-2-yl]-5Z-heptenoic acid | 0.50 (methylene chloride: methanol = 10:1) | 5.42(2H, m), 5.00(1H, broad), 3.72(1H, broad), 3.01(2H, dt), 2.70–1.35(18H), 1.21(3H, s), 1.02(3H, s), 0.94(3H, t), 0.83(1H, d) | 385(M⁺), 367, 316, 298 | pale yellow oil |
| 3 (k) | —(CH₂)₅CH₃ | 7-[(1S,2S,3S,5R)-3-hexyl sulfonylamino-6, 6-dimethyl bicyclo[3.1.1]heptan-2-yl]- | 0.45 (methylene chloride: | 5.46(2H, m), 4.94(1H, d) 3.72(1H, m), 3.02(2H, m) | 413(M⁺), 395, 334, 326 | pale yellow oil |

TABLE III-continued

| | | 5Z-heptenoic acid | methanol = 10:1 | | | |
|---|---|---|---|---|---|---|
| 3 (l) | —(CH₂)₇CH₃ | 7-[(1S,2S,3S,5R)-3-octyl sulfonylamino-6, 6-dimethyl bicyclo[3.1.1]heptan-2-yl]-5Z-heptenoic acid | 0.45 (methylene chloride: methanol = 10:1) | 5.42(2H, m), 3.72(1H, m), 3.00(2H, m) | 441(M⁺), 423, 372, 354 | pale yellow oil |

| Example No. | —R²—R³ | Name | TLC (Rf) | IR (ν cm⁻¹) |
|---|---|---|---|---|
| 3 (m) | 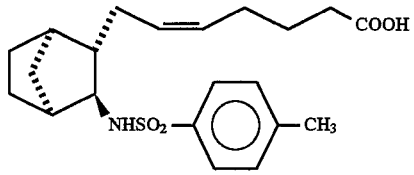 | 7-[(1S,2S,3S,5R)-3-(2-phenylethyl)sulfonyl amino-6, 6-dimethylbicyclo[3.1.1]heptan-2-yl]-5Z-heptenoic acid | 0.24 (ethyl acetate: hexane = 1:1) | 3272, 1708, 1604, 1455, 1306, 1236, 1147, 1062 |
| 3 (n) | | 7-[(1S,2S,3S,5R)-3-(2-cyclohexylethyl)sulfonyl amino-6, 6-dimethylbicyclo[3.1.1]heptan-2-yl]-5Z-heptenoic acid | 0.25 (ethyl acetate: hexane = 2:3) | 3271, 2926, 1708, 1450, 1309 |

Example 4

7-[(1R,2S,3S,4S)-3-tosylaminobicyclo[2.2.1]heptan-2-yl]-5Z-heptenoic acid

Potassium tert-butoxide (740 mg) was added to a suspension 4-carboxybutyltriphenylphosphonium bromide (1.33 g) in toluene (10 ml). The mixture was stirred for 40 minutes at 80° C. The reaction solution was cooled at 0° C. A solution of [(1R,2S,3S,4S)-3-tosylaminobicyclo[2.2.1] heptan-2-yl]acetaldehyde (the compound was described as reference example 20 in specification of the U.S. Pat. No. 5,168,101) (270 mg) in toluene (10 ml) was dropped to the reaction solution. The mixture was stirred for 15 minutes at 0° C. The reaction mixture was poured into ice-water and extracted with ether. The water layer was acidified by adding 1N hydrochloric acid (10 ml) and extracted with ethyl acetate. The extract was dried over magnesium sulfate and concentrated under reduced pressure. The residue was purified by column chromatography on silica gel (methylene chloride:methanol=25:1) to give the title compound (222 mg) having the following physical data.

TLC: Rf 0.45 (methylene chloride:methanol=10:1);

NMR: δ 7.75(2H, d), 7.28(2H, d), 5.26(2H, m), 5.11(1H, d), 3.00(1H), 2.42(3H, s), 2.37(2H, t), 2.16~0.87(15H);

MS: m/e 391 (M⁺), 373;

Feature: white powder.

Example 5

By the same procedure as in example 4, using corresponding starting materials and various phosphonium salts, purposed compounds shown in following table IV and table V were given.

TABLE IV

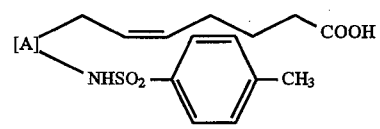

| Example No. | [A] | Name | TLC (Rf) | NMR (δ) | MS (m/e) | Feature |
|---|---|---|---|---|---|---|
| 5 (a) | (±) | 7-[(2S*,3S*)-3-tosylamino bicyclo[2.2.2]octan-2-yl]-5Z-heptenoic acid | 0.45 (methylene chloride: methanol = 10:1) | 7.75(2H, d), 7.26(2H, d), 5.28(3H, m), 2.86(1H, t), 2.42(3H, s), 2.37(2H, t), 2.20~1.10(17H) | 405(M⁺), 387, 361 | white wax |

TABLE IV-continued

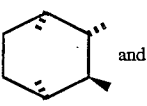

| Example No. | [A]⟨ | Name | TLC (Rf) | NMR (δ) | MS (m/e) | Feature |
|---|---|---|---|---|---|---|
| 5 (b) | mixture of  and 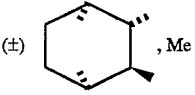 | a mixture of 7-[(1R,2S,3S, 4S)-3-tosylaminobicyclo[2.2.1] heptan-2-yl]-5Z-heptenoic acid and an isomer of (1S, 2S,3S,4R) | 0.45 (methylene chloride: methanol = 10:1) | 7.74(2H, d), 7.28(2H, d), 5.28(2H, m), 5.15(1H, d), 3.00(1H, m), 2.43(3H, s), 2.35(2H, t), 2.16–0.87(15H) | 391(M+), 373, 363, 345, 289 | colorless oil |

TABLE V

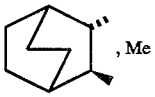

| Example No. | [A]⟨ , R² | Name | TLC (Rf) | IR (ν cm⁻¹) |
|---|---|---|---|---|
| 5 (c) | (±) 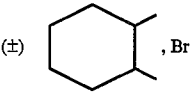 , Me | 7-[(1R*,2S*,3S*,4S*)-3-tosylamino bicyclo[2.2.1]heptan-2-yl]-5Z-heptenoic acid | 0.45 (methylene chloride:methanol = 10:1) | 3270, 2950, 1705, 1600, 1420, 1320, 1150, 1090, 815 |
| 5 (d) | 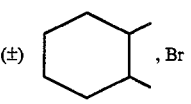 , Me | 7-[(2S,3S)-3-tosylaminobicyclo[2.2.2] octan-2-yl]-5Z-heptenoic acid | 0.50 (methylene chloride:methanol = 10:1) | (solution of chloroform) 3270, 2950, 1720, 1420, 1330, 1170, 1105 |
| 5 (e) | (±)  , Br more polar | 7-[2-(4-bromophenylsulfonylamino) cyclohexyl]-5Z-heptenoic acid | 0.42 (methylene chloride:methanol = 9:1) | (KBr disk method) 3280, 2920, 1690, 1430, 1330, 1155, 1080, 1065 |
| 5 (f) | (±)  , Br less polar | 7-[2-(4-bromophenylsulfonylamino) cyclohexyl]-5Z-heptenoic acid | 0.42 (methylene chloride:methanol = 9:1) | (KBr disk method) 3280, 2920, 1690, 1430, 1330, 1155, 1080, 1065 |
| 5 (g) | (±) , Me | 7-[(1R*,2S*)-2-tosylaminocyclopentyl- 5Z-heptenoic acid | 0.20 (ethyl acetate: hexane = 1:1) | 3260, 2940, 1705, 1600, 1430, 1320, 1155, 1095, 910 |
| 5 (h) | (±) , Br | 7-[(1R*,2S*)-2-(4-bromophenylsulfonyl amino)cyclopentyl]-5Z-heptenoic acid | 0.20 (ethyl acetate: hexane = 1:1) | (KBr disk method) 3260, 2940, 1690, 1570, 1430, 1380, 1330, 1155, 1090, 1005, 905 |

TABLE V-continued

| Example No. | Structure | Name | TLC (Rf) | IR (ν cm⁻¹) |
|---|---|---|---|---|
| 5 (i) | 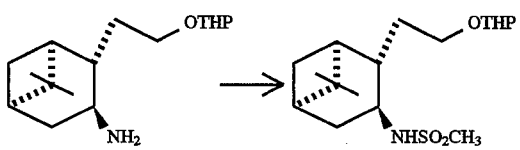 | 6-[(1S,2S,3S,4R)-3-(4-bromophenyl sulfonylaminomethyl)bicyclo[2.2.1] heptan-2-yl]-5Z-hexenoic acid | 0.44 (ethyl acetate: hexane = 1:1) | (KBr disk method) 3260, 2920, 1680, 1310, 1140 |

Reference Example 1

Synthesis of (1S,2S,3S,5R)-3-mesylamino-2-[2-(2-tetrahydropyranyl oxy)ethyl]-6,6-dimethylbicyclo[3.1.1] heptane Triethylamine (1.9 ml) was added to a solution of (1S, 2S,3S,5R)-3-amino-2-[2-(2-tetrahydropyranyloxy)ethyl]-6, 6-dimethylbicyclo[3.1.1]heptane (3.25 g) in methylene chloride (30 ml). The reaction solution was cooled. To the above solution, mesyl chloride (1.0 ml) was dropped slowly. The reaction solution was allowed to stand for 1 hour. The reaction solution was extracted with methylene chloride. The organic layer was washed with brine, dried over magnesium sulfate and concentrated under reduced pressure. The residue was purified by column chromatography on silica gel (hexane-ethyl acetate) to give the title compound (3.05 g) having the following physical data.

TLC: Rf 0.50 (hexane:ethyl acetate=2:1);
MS: m/e 346, 277, 268, 262.

Reference Example 2

Synthesis of (1S,2S,3S,5R)-3-[2-(4-chlorophenyl)-2-hydroxyethylsulfonyl amino]-2-[2-(2-tetrahydropyranyloxy)ethyl]-6,6-dimethylbicyclo[3.1.1] heptane

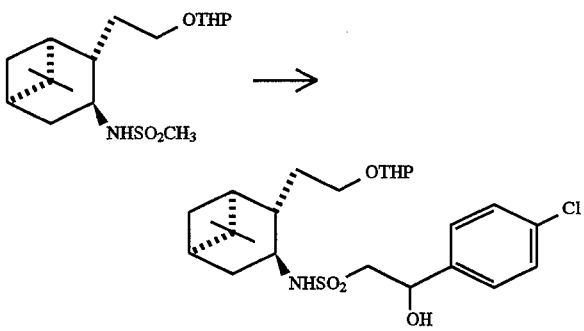

The compound prepared in reference example 1 (72.1 mg) was dissolved into the mixture of ether (1 ml) and tetramethylethylenediamine (0.22 ml) in dried container. A solution of n-butyl lithium in n-hexane (1.62M, 0.45 ml) was added slowly to the reaction solution at room temperature. The reaction solution was stirred for 2 hours. A solution of 4-chlorobenzaldehyde (68.8 mg) in ether (1 ml) was added to the above solution. The mixture was stirred for 30 minutes. A saturated aqueous solution of ammonium chloride was added to the reaction solution. The mixture was allowed to stand for 5 minutes and extracted with a mixture solvent of n-hexane-ethyl acetate (1:1). The organic layer was washed with brine, dried over magnesium sulfate and concentrated under reduced pressure. The residue was purified by column chromatography on silica gel (hexane-ethyl acetate) to give the title compound (82 mg) having the following physical data.

TLC: Rf 0.60 (hexane:ethyl acetate=3:2);

MS: m/e 400, 382, 332, 305.

Reference Example 3

Synthesis of (1S,2S,3S,5R)-3-[2-(4-chlorophenyl) vinylsulfonylamino]-2-[2-(2-tetrahydropyranyloxy)ethyl]-6,6-dimethylbicyclo[3.1.1]heptane

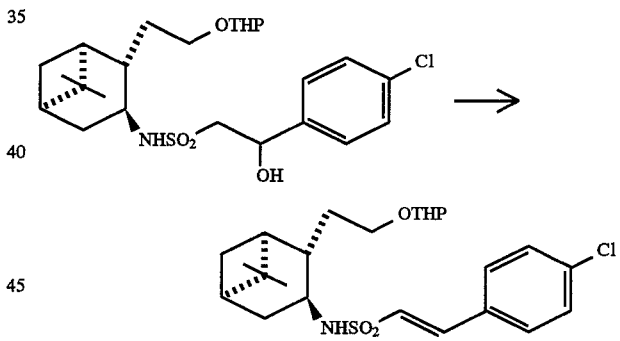

A mixture of the solution of the compound prepared in reference example 2 (258 mg) in methylene chloride (5 ml) and triethylamine (0.25 ml) was cooled. Mesyl chloride was dropped slowly to the above mixture,. Ice-bath was removed. The mixture was stirred for 30 minutes. Water was added to the reaction solution. The above solution was extracted with methylene chloride. The organic layer was washed with brine, dried over magnesium sulfate and concentrated under reduced pressure. The residue was purified by column chromatography on silica gel (hexane ethyl acetate) to give the title compound (232 mg).

Reference Example 4

Synthesis of (1S,2S,3S,5R)-3-[2-(4-chlorophenyl) vinylsulfonylamino]-2-(2-hydroxyethyl)-6,6-dimethylbicyclo[3.1.1]heptane

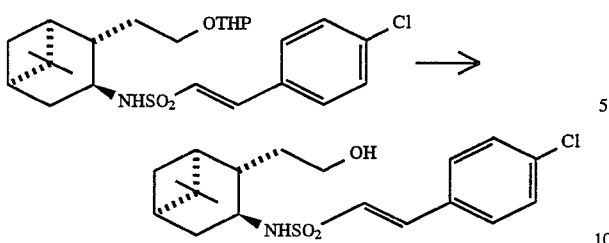

p-Toluenesulfonic acid (10 mg) was added to a solution of the compound prepared in reference example 3 (232 mg) in methanol (1.5 ml). The mixture was stirred for 1 hour at room temperature. Triethylamine was added to the reaction solution. The mixture was concentrated under reduced pressure. The residue was purified by column chromatography on silica gel (hexane-ethyl acetate) to give the title compound (187 mg) having the following physical data.

TLC: Rf 0.25 (hexane:ethyl acetate=3:2);
MS: m/e 384, 368, 314, 298, 270.

Reference Example 5

Synthesis of (1S,2S,3S,5R)-3-[2-(4-chlorophenyl)vinylsulfonylamino]-2-formylmethyl-6,6-dimethylbicyclo[3.1.1]heptane

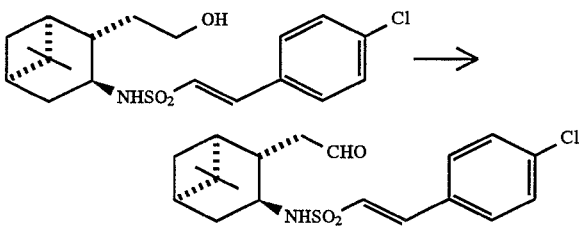

A solution of oxalyl chloride (0.07 ml) in methylene chloride (2 ml) was cooled at −70° C. To the above solution, a solution of DMSO (0.07 ml) in methylene chloride (2 ml) was dropped. The mixture was stirred for 10 minutes. A solution of the compound prepared in reference example 4 in methylene chloride (1 ml) was added to the reaction solution at same temperature. The mixture was stirred for 30 minutes. Triethylamine (0.25 ml) was added to the reaction solution. Dry ice-bath was removed. The mixture was stirred for 30 minutes and extracted with ether. The organic layer was washed with water and brine, dried over magnesium sulfate and concentrated under reduced pressure to give the title compound.

Example 6

Synthesis of 7-[(1S,2S,3S,5R)-3-[2-(4-chlorophenyl)vinylsulfonylamino]-6,6-dimethylbicyclo[3.1.1]heptan-2-yl]-5Z-heptenoic acid

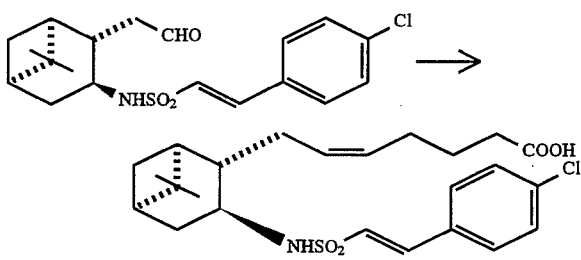

4-carboxybutyltriphenylphosphonium bromide (343 mg) and potassium t-butoxide (177 mg) was dissolved into THF (5 ml). The mixture was stirred for 10 minutes. A solution of the compound prepared in reference example 5 (113 mg) in THF (3 ml) was dropped to the reaction solution. The mixture was stirred for 1 hour. Water was added to the above mixture. The mixture solvent of ether-hexane (1:1) was added to the reaction solution. The above solution was separated. The water layer was acidified by adding 1N hydrochloride. The mixture was extracted with ethyl acetate. The organic layer was washed with brine, dried over magnesium sulfate and concentrated under reduced pressure. The residue was purified by column chromatography on silica gel (hexane-ethyl acetate) to give the title compound (105 mg) having the following physical data.

TLC: Rf 0.25 (hexane:ethyl acetate=1:1);
MS: m/e 465, 447, 396, 378;
IR: ν 3271, 2922, 1708, 1309, 1144 cm$^{-1}$.

Example 6(1)~6(26)

By the same procedure as in reference example 1~5 and example 6, using corresponding starting materials and corresponding phosphonium slats, the title compound having the physical data shown in table VI, VII and VIII were given.

TABLE VI

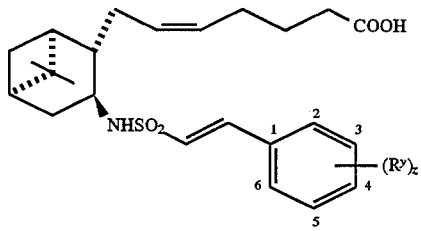

| Example No. | (R$^Y$)x | Name | TLC (Rf) | IR (ν cm$^{-1}$) |
|---|---|---|---|---|
| 6 (1) | 3-F | 7-[(1S, 2S, 3S, 5R)-3-[2-(3-fluorophenyl)vinylsulfonylamino]-6,6-dimethylbicyclo[3.1.1]heptan-2-yl]-5Z-heptenoic acid | 0.25 (ethyl acetate:hexane = 1:1) | 3271, 2922, 1709, 1584, 1447, 1142 |
| 6 (2) | 4-F | 7-[(1S, 2S, 3S, 5R)-3-[2-(4-fluorophenyl)vinylsulfonylamino]-6,6-dimethylbicyclo | 0.30 (ethyl | 3272, 2922, 1709, 1602, 1510, 1143 |

TABLE VI-continued

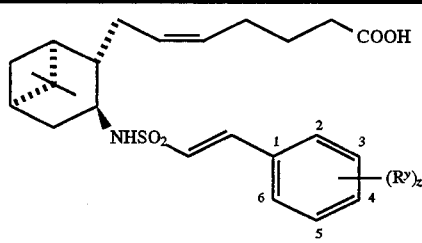

| Example No. | (R^Y)x | Name | TLC (Rf) | IR (ν cm⁻¹) |
|---|---|---|---|---|
| | | [3.1.1]heptan-2-yl]-5Z-heptenoic acid | acetate:hexane = 1:1) | |
| 6 (3) | 4-Br | 7-[(1S, 2S, 3S, 5R)-3-[2-(4-bromophenyl) vinylsulfonylamino]-6,6-dimethylbicyclo [3.1.1]heptan-2-yl]-5Z-heptenoic acid | 0.20 (ethyl acetate:hexane = 1:1) | 3272, 2917, 1708 |
| 6 (4) | 4-CH₃O | 7-[(1S, 2S, 3S, 5R)-3-[2-(4-methoxyphenyl) vinylsulfonylamino]-6,6-dimethylbicyclo [3.1.1]heptan-2-yl]-5Z-heptenoic acid | 0.30 (ethyl acetate:hexane = 1:1) | 3272, 2921, 1708, 1423, 1259 |
| 6 (5) | 4-CH₃ | 7-[(1S, 2S, 3S, 5R)-3-[2-(4-methylphenyl) vinylsulfonylamino]-6,6-dimethylbicyclo [3.1.1]heptan-2-yl]-5Z-heptenoic acid | 0.20 (ethyl acetate:hexane = 1:1) | 3272, 2918, 1708, 1441, 1142 |
| 6 (6) | 3-CH₃O | 7-[(1S, 2S, 3S, 5R)-3-[2-(3-methoxyphenyl) vinylsulfonylamino]-6,6-dimethylbicyclo [3.1.1]heptan-2-yl]-5Z-heptenoic acid | 0.21 (ethyl acetate:hexane = 1:1) | 3272, 2921, 1708, 1580, 1434, 1142 |
| 6 (7) | 3-Br | 7-[(1S, 2S, 3S, 5R)-3-[2-(3-bromophenyl) vinylsulfonylamino]-6,6-dimethylbicyclo [3.1.1]heptan-2-yl]-5Z-heptenoic acid | 0.25 (ethyl acetate:hexane = 1:1) | 3272, 2921, 1708, 1439, 1143 |
| 6 (8) | 2,6-diCH₃ | 7-[(1S, 2S, 3S, 5R)-3-[2-(2,6-dimethylphenyl) vinylsulfonylamino]-6,6-dimethylbicyclo [3.1.1]heptan-2-yl]-5Z-heptenoic acid | 0.36 (ethyl acetate:hexane = 1:1) | 3271, 2922, 1709, 1441, 1307, 1142 |
| 6 (9) | 3-CH₃ | 7-[(1S, 2S, 3S, 5R)-3-[2-(3-methylphenyl) vinylsulfonylamino]-6,6-dimethylbicyclo [3.1.1]heptan-2-yl]-5Z-heptenoic acid | 0.30 (ethyl acetate:hexane = 1:2) | 3272, 2922, 1708, 1440, 1331, 1141 |
| 6 (10) | 3-Cl | 7-[(1S, 2S, 3S, 5R)-3-[2-(3-chlorophenyl) vinylsulfonylamino]-6,6-dimethylbicyclo [3.1.1]heptan-2-yl]-5Z-heptenoic acid | 0.35 (ethyl acetate:hexane = 1:2) | 3272, 2922, 1708, 1432, 1332, 1143 |
| 6 (11) | 3-CF₃ | 7-[(1S, 2S, 3S, 5R)-3-[2-(3-trifluoromethyl phenyl)vinylsulfonylamino]-6,6-dimethyl bicyclo[3.1.1]heptan-2-yl]-5Z-heptenoic acid | 0.30 (ethyl acetate:hexane = 2:3) | 3280, 2925, 1709, 1440, 1333, 1133 |
| 6 (12) | H | 7-[(1S, 2S, 3S, 5R)-3-(2-phenylvinylsulfonyl amino)-6,6-dimethylbicyclo[3.1.1]heptan-2-yl]-5Z-heptenoic acid | 0.30 (ethyl acetate:hexane = 1:2) | 3339, 2929, 1679, 1453, 1302, 1142 |

TABLE VII

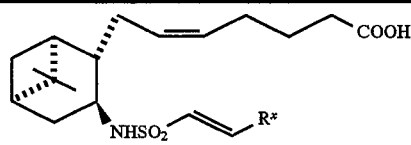

| Example No. | R^x | Name | TLC (Rf) | IR (ν cm⁻¹) |
|---|---|---|---|---|
| 6 (13) | cyclohexyl | 7-[(1S, 2S, 3S, 5R)-3-(2-cyclohexylvinylsulfonylamino)-6,6-dimethylbicyclo[3.1.1]heptan-2-yl]-5Z-heptenoic acid | 0.25 (ethyl acetate:hexane = 2:3) | 3271, 2927, 1709, 1450, 1337, 1145 |
| 6 (14) | —C₄H₉ | 7-[(1S, 2S, 3S, 5R)-3-(5E-hexenylsulfonylamino)-6,6-dimethylbicyclo[3.1.1]heptan-2-yl]-5Z-heptenoic acid | 0.30 (ethyl acetate:hexane = 1:2) | 3339, 2929, 1679, 1453, 1302, 1142 |

TABLE VII-continued

[Structure: bicyclic heptane with NHSO2-CH=CH-R* substituent and CH2-CH=CH-CH2-CH2-CH2-COOH chain]

| Example No. | Structure | Name | TLC (Rf) | IR (ν cm⁻¹) |
|---|---|---|---|---|
| 6 (15) | [Structure with N(Me)-SO2-CH=CH-phenyl] | 7-[(1S, 2S, 3S, 5R)-3-(2-phenylvinyl sulfonyl-N-methylamino)-6,6-dimethyl bicyclo[3.1.1]heptan-2-yl]-5Z-heptenoic acid | 0.24 (ethyl acetate:hexane = 1:1) | 1708, 1616, 1577, 1450, 1336, 1142, 973 |
| 6 (16) | [Structure with NHSO2-CH=CH-phenyl, 4Z chain] | 7-[(1S, 2S, 3S, 5R)-3-(2-phenylvinyl sulfonylamino)-6,6-dimethylbicyclo[3.1.1]heptan-2-yl]-4Z-heptenoic acid | 0.21 (ethyl acetate:hexane = 1:1) | 3271, 1713, 1624, 1577, 1449, 1317, 1142, 1059, 972 |
| 6 (26) | [Structure with NHSO2-CH=CH-phenyl, 5E chain] | 7-[(1S, 2S, 3S, 5R)-3-(2-phenylvinyl sulfonylamino)-6,6-dimethylbicyclo[3.1.1]heptan-2-yl]-5E-heptenoic acid | 0.13 (ethyl acetate:hexane = 1:1) | (KBr disk method) 3273, 2921, 1708, 1450, 1328, 1143 |

TABLE VIII

TxA with R¹⁰⁰—COOH and R³⁰⁰—NHSO2-CH=CH-phenyl

| Example No. | TxA with R¹⁰⁰— and R³⁰⁰— | Name | TLC (Rf) | IR (ν cm⁻¹) |
|---|---|---|---|---|
| 6 (17) | [bicyclo[2.2.1]heptane structure] | 7-[(1R, 2S, 3S, 4S)-3-(2-phenylvinyl sulfonylamino)bicyclo[2.2.1]heptan-2-yl]-5Z-heptenoic acid | 0.24 (ethyl acetate:hexane = 1:1) | 3274, 1708, 1624, 1577, 1450, 1318, 1146, 973 |
| 6 (18) | [bicyclo[2.2.1]heptane with CH2- structure] | 6-[(1S, 2S, 3R, 4R)-3-(2-phenylvinyl sulfonylaminomethyl)bicyclo[2.2.1]heptan-2-yl]-5Z-hexenoic acid | 0.13 (ethyl acetate:hexane = 1:1) | 3274, 1708, 1623, 1577, 1450, 1418, 1320, 1147, 972 |
| 6 (19) | [cyclohexyl (±) structure] | 7-[(1R*, 2S*)-2-(2-phenylvinylsulfonyl amino)cyclohexyl]-5Z-heptenoic acid | 0.20 (ethyl acetate:hexane = 1:1) | 3272, 1708, 1624, 1577, 1496, 1449, 1319, 1241, 1195, 1148, 1071, 971 |
| 6 (20) | [cyclohexyl (±) structure] | 7-[(1S*, 2S*)-2-(2-phenylvinylsulfonyl amino)cyclohexyl]-5Z-heptenoic acid | 0.17 (ethyl acetate:hexane = 1:1) | 3292, 1708, 1623, 1577, 1451, 1326, 1148, 1005 |

TABLE VIII-continued

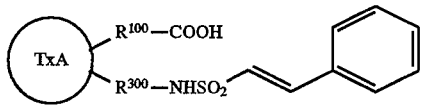

| Example No. | | Name | TLC (Rf) | IR (ν cm⁻¹) |
|---|---|---|---|---|
| 6 (21) | | 6-[(1R*, 3R*)-3-(2-phenylvinylsulfonyl amino)cyclohexyl]-5Z-hexenoic acid | 0.30 (ethyl acetate:hexane = 1:1) | 3306, 2930, 1708, 1450, 1318, 1146 |
| 6 (22) | | 6-[(1S, 3R)-3-(2-phenylvinylsulfonyl-amino)cyclopentyl]-5Z-hexenoic acid | 0.28 (ethyl acetate:hexane = 1:1) | 3307, 2930, 1708, 1451, 1303 |
| 6 (23) | | 6-[(1R, 3R)-3-(2-phenylvinylsulfonyl amino)cyclopentyl]-5Z-hexenoic acid | 0.25 (ethyl acetate:hexane = 1:1) | 3307, 2990, 1707, 1451, 1317 |
| 6 (24) | | 6-[(1S, 3S)-3-(2-phenylvinylsulfonyl amino)cyclopentyl]-5Z-hexenoic acid | 0.25 (ethyl acetate:hexane = 1:1) | 3272, 2952, 1708, 1449, 1318, 1145 |
| 6 (25) | | 6-[(1R, 3S)-3-(2-phenylvinylsulfonyl amino)cyclopentyl]-5Z-hexenoic acid | 0.28 (ethyl acetate:hexane = 1:1) | 3307, 2930, 1708, 1451, 1303 |

Example 7

Synthesis of 7-[(1S,2S,3S,5R)-3-(2-phenylvinylsulfonylamino)-6,6-dimethyl bicyclo[3.1.1] heptan-2-yl]-5Z-heptenoic acid methyl ester

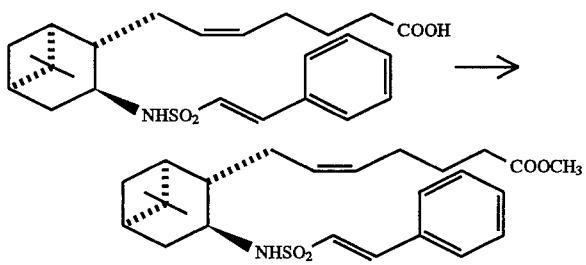

To a solution of the compound prepared in example 6(12) (97 mg) in methanol (5 ml), a solution of diazomethane in ether was added till the mixture showed a yellow color at 0° C. The reaction mixture was concentrated under reduced pressure. The residue was purified by column chromatography on silica gel (ethyl acetate-hexane) to give the title compound (90 mg) having the following physical data.

TLC: Rf 0.38 (ethyl acetate:hexane=1:2);

IR: ν3274, 1738, 1624, 1577, 1438, 1332, 1146, 1061, 973 cm⁻¹.

Example 8

Synthesis of 7-[(1S,2S,3S,5R)-3-(2,2-diphenylvinylsulfonylamino)-6,6-dimethylbicyclo[3.1.1] heptan-2-yl]-5Z-heptenoic acid methyl ester

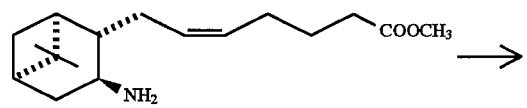

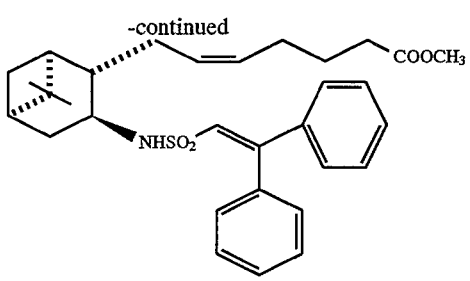

7-[(1S,2S,3S,5R)-3-amino-6,6-dimethylbicyclo[3.1.1]heptan-2yl]-5Z-heptenoic acid methyl ester (The compound was described as reference example 14 in specification of the U.S. Pat. No. 4,792,550; 145 mg) and triethylamine (0.21 ml) were dissolved into methylene chloride (5 ml) and the mixture-was cooled with ice-bath. 2,2-Diphenylvinylsulfonyl chloride (188 mg) was added to the above solution. The mixture was stirred for 2 hours at room temperature. The reaction mixture was poured into 1N hydrochloric acid (5 ml) and extracted with ethyl acetate. The organic layer was washed with saturated sodium bicarbonate and brine, successively, dried over magnesium sulfate and concentrated under reduced pressure. The residue was purified by column chromatography on silica gel (3% ethyl acetate/hexane) to give the title compound (203 mg) having the following physical data.

TLC: Rf 0.29 (hexane:ethyl acetate=3:1)

Example 9

Synthesis of 7-[(1S,2S,3S,5R)-3-(2,2-diphenylvinylsulfonylamino)-6,6-dimethylbicyclo[3.1.1]heptan-2-yl]-5Z-heptenoic acid To a mixed solution of dimethoxyethane (3 ml) and methanol (1.5 ml) of the compound prepared in example 8 (191 mg), 2N sodium hydride solution (1 ml) was added. The mixture was stirred for 4 hours at room temperature. After solvent was distilled off the reaction mixture, ice and 1N hydrochloric acid (2 ml) were added to the residue. The above solution was extracted with ethyl acetate. The organic layer was washed with water and brine, successively, dried over magnesium sulfate and concentrated under reduced pressure. The residue was purified by column chromatography on silica gel (hexane:ethyl acetate=2:1→1:2 (0.1% acetic acid)) to give the title compound (101 mg) having the following physical data.

TLC: Rf 0.21 (hexane:ethyl acetate=1:1);

NMR: δ 7.48–7.22 (10H, m), 6.87 (1H, s), 5.49–5.26 (2H, m), 4.58 (1H, d), 3.73 (1H, m), 2.60–1.84 (10H, m), 1.80–1.47 (4H, m), 1.18 (3H, s), 0.98 (3H, s), 0.70 (1H, d).

Formulation Example 1: Preparation of Tablets

The following compounds were admixed in conventional method and punched out to obtain 100 tablets each containing 100 mg of active ingredient.

| | |
|---|---|
| 7-[(1S,2S,3S,5R)-3-tosylamino-6,6-dimethylbicyclo[3.1.1]heptan-2-yl]-5Z-heptenoic acid | 10 g |
| Cellulose calcium glycolate (disintegrating agent) | 200 mg |
| Magnesium stearate (lubricating agent) | 100 mg |
| Micro crystalline cellulose | 9.7 g |

Formulation Example 2: Preparation of Tablets

The following compounds were admixed in conventional method and punched out to obtain 100 tablets each containing 100 mg of active ingredient.

| | |
|---|---|
| 7-[(1S,2S,3S,5R)-3-[2-(4-chlorophenyl)vinylsulfonylamino]-6,6-dimethylbicyclo[3.1.1]heptan-2-yl]-5Z-heptenoic acid | 10 g |
| Cellulose calcium glycolate (disintegrating agent) | 200 mg |
| Magnesium stearate (lubricating agent) | 100 mg |
| Micro crystalline cellulose | 9.7 g |

Formulation Example 3: Preparation of Injections

7-[(1S,2S,3S,5R)-3-tosylamino-6,6-dimethylbicyclo[3.1.1]heptan-2-yl]-5Z-heptenoic acid (5 g) and mannitol (50 g) were dissolved by adding distilled water. Then, distilled water was added thereto to make the total volume 500 ml. The solution was filtrated by a bacteria-retaining filter. The solution was placed in 5 ml portion in 10 ml vial in usual way and freeze-dried to obtain 100 vials each containing 50 mg of active ingredient.

Formulation Example 4: Preparation of Injections

7-[(1S,2S,3S,5R)-3-[2-(4-chlorophenyl)vinylsulfonylamino]-6,6-dimethylbicyclo[3.1.1]heptan-2-yl]-5Z-heptenoic acid (5 g) and mannitol (50 g) were dissolved by adding distilled water. Then, distilled water was added thereto to make the total volume 500 ml. The solution was filtrated by a bacteria-retaining filter. The solution was placed in 5 ml portion in 10 ml vial in usual way and freeze-dried to obtain 100 vials each containing 50 mg of active ingredient.

What is claimed is:

1. Carbocyclic sulfonamides of the formula:

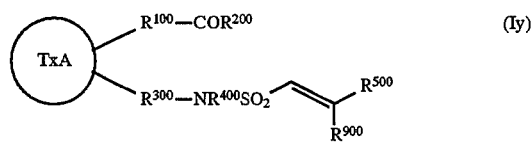

(Iy)

wherein

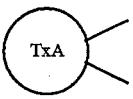

is i)

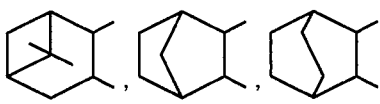

or ii)

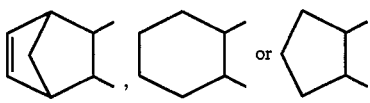

$R^{100}$ is C4–7 alkylene or C4–7 alkenylene;

$R^{200}$ is hydroxy, C1–20 alkoxy or $NR^{230}R^{240}$ in which $R^{230}$ and $R^{240}$ each, independently, is hydrogen, C1–4 alkyl or $NR^{230}R^{240}$ is amino acid residue;

$R^{300}$ is a single bond or C1–4 alkylene;

$R^{400}$ is hydrogen or C1–4 alkyl;

$R^{500}$ and $R^{900}$ each, independently, is i) 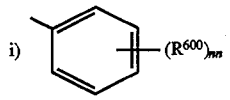

in which $R^{600}$ is hydrogen, C1–4 alkyl, C1–4 alkoxy, hydroxy, halogen, trifluoromethyl, nitro;

nn is 1, 2 or 3;

ii) 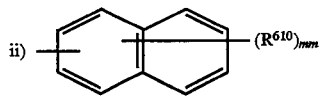

in which $R^{610}$ is hydrogen, C1–4 alkyl, C1–4 alkoxy, hydroxy, halogen, trifluoromethyl, nitro;

mm is 1, 2 or 3;

iii) 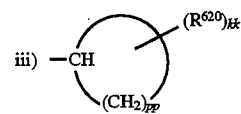

in which $R^{620}$ is hydrogen, C1–4 alkyl, C1–4 alkoxy, hydroxy, halogen, trifluoromethyl, nitro;

kk is 1, 2 or 3;

pp is 3, 4, 5, or 6;

iv) C1–7 alkyl or v) hydrogen;

cyclodextrin clathrates thereof or non-toxic salts thereof.

2. A compound according to claim 1, wherein

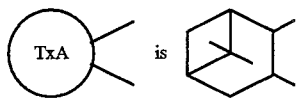

3. A compound according to claim 1, wherein

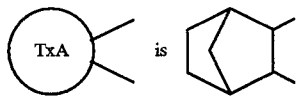

4. A compound according to claim 1, wherein

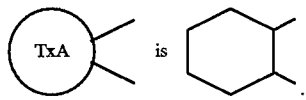

5. A compound according to claim 1, wherein $R^{100}$ is pentenylene or hexenylene, $R^{300}$ is a single bond or methylene.

6. A compound according to claim 2, wherein $R^{500}$ is the formula:

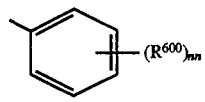

wherein all the symbols are the same meaning as defined in claim 1, and $R^{900}$ is hydrogen or the formula:

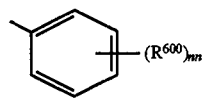

wherein all the symbols are the same meaning as defined in claim 1.

7. A compound according to claim 1, wherein $R^{500}$ is

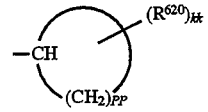

wherein all the symbols are the same meaning as hereinbefore defined, or C1–7 alkyl and $R^{900}$ is hydrogen.

8. A compound according to claim 1, which is

7-[3-[2-(4-chlorophenyl)vinylsulfonylamino]-6,6-dimethylbicyclo[3.1.1]heptan-2-yl]-5Z-heptenoic acid methyl ester, 7-[3-(2-phenylvinylsulfonyl-N-methylamino)-6,6-dimethylbicyclo[3.1.1]heptan-2-yl]-5Z-heptenoic acid, 7-[3-(2-phenylvinylsulfonylamino)-6,6-dimethyl bicyclo[3.1.1]heptan-2-yl]-5Z-heptenoic acid, 7-[3-[2-(3-fluorophenyl)vinylsulfonylamino]-6,6-dimethylbicyclo[3.1.1]heptan-2-yl]-5Z-heptenoic acid, 7-[3-[2-(4-fluorophenyl)vinylsulfonylamino]-6,6-dimethylbicyclo[3.1.1]heptan-2-yl]-5Z-heptenoic acid, 7-[3-[2-(4-bromophenyl)vinylsulfonylamino]-6,6-dimethylbicyclo[3.1.1]heptan-2-yl]-5Z-heptenoic acid, 7-[3-[2-(4-chlorophenyl)vinylsulfonylamino]-6,6-dimethylbicyclo[3.1.1]heptan-2-yl]-5Z-heptenoic acid, 7-[3-[2-(4-metoxyphenyl)vinylsulfonylamino]-6,6-dimethylbicyclo[3.1.1]heptan-2-yl]-5Z-heptenoic acid, 7-[3-[2-(4-methylphenyl)vinylsulfonylamino]-6,6-dimethylbicyclo[3.1.1]heptan-2-yl]-5Z-heptenoic acid, 7-[3-[2-(3-metoxyphenyl)vinylsulfonylamino]-6,6-dimethylbicyclo[3.1.1]heptan-2-yl]-5Z-heptenoic acid, 7-[3-[2-(3-bromophenyl)vinylsulfonylamino]-6,6-dimethylbicyclo[3.1.1]heptan-2-yl]-5Z-heptenoic acid, 7-[3-[2-(2,6-dimethylphenyl)vinylsulfonylamino]-6,6-dimethylbicyclo[3.1.1]heptan-2-yl]-5Z-heptenoic acid, 7-[3-[2-(3-methylphenyl)vinylsulfonylamino]-6,6-dimethylbicyclo[3.1.1]heptan-2-yl]-5Z-heptenoic acid, 7-[3-[2-(3-chlorophenyl)vinylsulfonylamino]-6,6-dimethylbicyclo[3.1.1]heptan-2-yl]-5Z-heptenoic acid, 7-[3-[2-(3-trifluoromethylphenyl)vinylsulfonylamino]-6,6-dimethylbicyclo[3.1.1]heptan-2-yl]-5Z-heptenoic acid, 7-[3-(2-phenylvinylsulfonylamino)-6,6-dimethylbicyclo[3.1.1]heptan-2-yl]-5Z-heptenoic acid, 7-[3-(2-phenylvinylsulfonylamino)-6,6-dimethylbicyclo[3.1.1]heptan-2-yl]-5E-heptenoic acid, 7-[3-(2,2-diphenylvinylsulfonylamino)-6,6-dimethylbicyclo[3.1.1]heptan-2-yl]-5Z-heptenoic acid, 7-[3-(2-cyclohexylvinylsulfonylamino)-6,6-dimethylbicyclo[3.1.1]heptan-2-yl]-5Z-heptenoic acid, 7-[3-(5Z-hexenylsulfonylamino)-6,6-dimethylbicyclo[3.1.1]heptan-2-yl]-5Z-heptenoic acid, 7-[3-(2-phenylvinylsulfonylamino)bicyclo[2.2.1]heptan-2-yl]-5Z-heptenoic acid, 7-[3-(2-phenylvinylsulfonylaminomethyl)bicyclo[2.2.1]heptan-2-yl]-5Z-hexenoic acid or 7-[2-(2-phenylvinylsulfonylamino)cyclohexyl]-5Z-heptenoic acid.

9. A compound according to claim 1, wherein

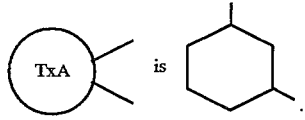

10. A compound according to claim 1, wherein

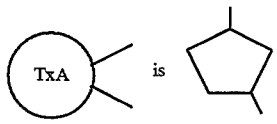

11. A compound according to claim 1, wherein $R^{100}$ is pentenylene, $R^{300}$ is a single bond, $R^{500}$ is

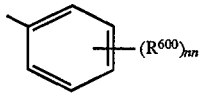

wherein all the symbols are the same meaning as defined in claim 1, and $R^{900}$ is hydrogen.

12. A compound according to claim 1, which is

6-[3-(2-phenylvinylsulfonylamino)cyclohexyl]-5Z-hexenoic acid or

6-[3-(2-phenylvinylsulfonylamino)cyclopentyl]-5Z-hexenoic acid.

13. A pharmaceutical composition for the treatment of abortion, pain, diarrhea, ansomnia, constipation, ulcer, gastritis or hypertension, or for induction of labor in pregnant female mammals, which comprises, as active ingredient, an effective amount of a carbocyclic sulfonamides of the formula (Iy) depicted in claim 1 or cyclodextrin clathrates thereof or non-toxic salts thereof, with a pharmaceutical carrier or coating.

14. The compound according to claim 2, wherein

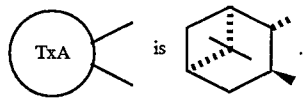

15. The compound according to claim 3, wherein

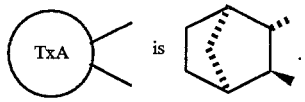

16. The compound according to claim 3, wherein

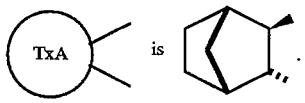

17. The compound according to claim 4, wherein

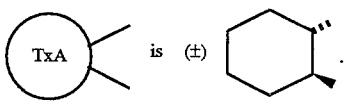

18. The compound according to claim 4, wherein

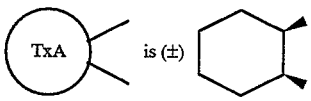

19. The compound according to claim 9, wherein

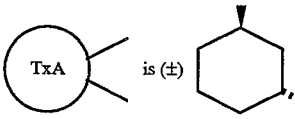

20. The compound according to claim 10, wherein

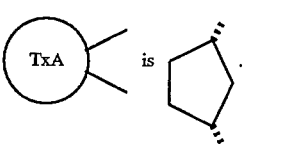

21. The compound according to claim 10, wherein

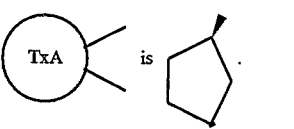

22. The compound according to claim 10, wherein 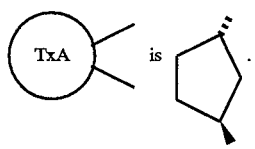.
23. The compound according to claim 10, wherein 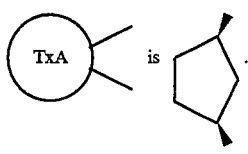.